United States Patent
Cywin et al.

(10) Patent No.: US 6,825,219 B2
(45) Date of Patent: Nov. 30, 2004

(54) SUBSTITUTED BENZIMIDAZOLE COMPOUNDS

(75) Inventors: Charles Cywin, Bethel, CT (US); Jinbo Lee, Southbury, MA (US); Steven S. Pullen, Danbury, CT (US); Gregory Paul Roth, New Milford, CT (US); Christopher Ronald Sarko, New Milford, CT (US); Roger John Snow, Danbury, CT (US); Noel Stewart Wilson, New Milford, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/288,362

(22) Filed: Nov. 5, 2002

(65) Prior Publication Data

US 2003/0144281 A1 Jul. 31, 2003

Related U.S. Application Data

(60) Provisional application No. 60/344,636, filed on Nov. 9, 2001.

(51) Int. Cl.$^7$ ............... A61K 31/4184; A61K 31/4439; C07D 235/30; C07D 401/12; C07D 409/12

(52) U.S. Cl. ...................... 514/338; 514/378; 514/388; 546/273.4; 548/304.7; 548/307.4; 548/248

(58) Field of Search ..................... 548/304.7, 307.4, 548/248; 546/273.4; 514/338, 388, 378

(56) References Cited

U.S. PATENT DOCUMENTS

| | | | |
|---|---|---|---|
| 3,401,171 A | * | 9/1968 | Craig et al. ............. 548/307.4 |
| 4,139,626 A | | 2/1979 | Beard |
| 4,191,764 A | | 3/1980 | Beard |
| 4,312,873 A | | 1/1982 | Beard |
| 5,141,950 A | | 8/1992 | Nakane et al. |
| 5,180,724 A | | 1/1993 | Bowles et al. |
| 5,270,148 A | | 12/1993 | Morigaki et al. |
| 5,541,339 A | | 7/1996 | Kelly et al. |
| 5,559,127 A | | 9/1996 | Hartman et al. |
| 5,616,537 A | | 4/1997 | Yokota et al. |
| 5,770,544 A | | 6/1998 | Yokota et al. |
| 2003/0125550 A1 | | 7/2003 | Blume et al. |
| 2003/0144286 A1 | | 7/2003 | Alexander et al. |

FOREIGN PATENT DOCUMENTS

| | | |
|---|---|---|
| CA | 1094061 | 3/1977 |
| CA | 1094061 | 1/1981 |
| CA | 2115737 | 8/1994 |
| WO | WO 99/24035 | 5/1999 |
| WO | WO 01/21634 A1 | 3/2001 |
| WO | WO 01/25238 | 4/2001 |
| WO | WO 01/70705 A1 | 9/2001 |
| WO | WO 03/030902 A1 | 4/2003 |

OTHER PUBLICATIONS

Thomas A. Waldmann; The IL–2/IL–2 receptor system: a target for rational immune intervention; Immunology Today, vol. 14, No. 6, 1993, pp 264–270.
Joanne L. Wright and Andrew Churg; Animal models of cigarette smoke–induced COPD (chronic obstructive pulmonary disease) Chest, Dec. 2002.
L.F. Neville, et al; Application of Differential Display to Isolate Novel Genes in Interleukin–2 Induced Adult Respiratory Distress Syndrome; Annals New York Academy of Sciences, pp257–271, year not available.
Karl W. Mollison, et al; Discovery of Ascomycin Analogs with Potent Topical but Weak Systemic Activity for Treatment of Inflammatory Skin Diseases,; Current Pharmaceutical Design, 1998, 4, pp 367–379.
Nobuo Hatamorl, et al Interleukin 2/Interleukin 2 receptor system in type 1 diabetes; Diabetes Research and Clinical Practices 7, (1989), S67–S–72.
P.L. Beck and J.L. Wallace, Cytokines in Inflammatory Bowel Diseases; Mediators of Inflammation 6, pp 95–103 (1997).
E. Peter Bosch, M.D.; Guillain–Barre Syndrome: An update of Acute Immune–Mediated Polyradiculoneuropathies; The Neurologist, vol. 4, No. 4, Jul. 1998, pp 211–226.
Jean E. Merrill; Autoimmune Disease and the Nervous System, Biochemical, Molecular, and Clinical Update; The Western Journal of Medicine, Jun. 1992, 156–6, pp 639–646.
Carol A. Feghali, and Timothy M. Wright; Cytokines in Acute and Chronic Inflammation; Frontiers in Bioscience 2, d12–26, Jan. 1, 1997.
Jan M. Agosti and Carol H. Sanes–Milller: Novel Therapeutic Approaches for Allergic Rhinitis; Immunology and Allergy Clinics of North America, vol. 20, No. 2, May 2000 pp 401–423.
K.F. Chung and P.J. Barnes; Cytokines in Asthma; Thorax, 1999, 54, 825–857.

(List continued on next page.)

Primary Examiner—Laura L. Stockton
(74) Attorney, Agent, or Firm—Raymond P. Raymond; Anthony P. Bottino; Timothy X. Witkowski

(57) ABSTRACT

Disclosed are substituted benzimidazole compounds of formula(I):

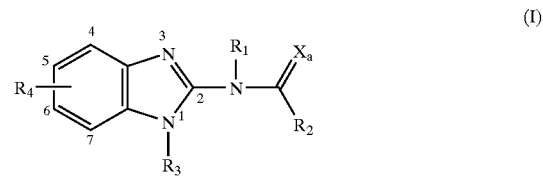

wherein $R_1$, $R_2$, $R_3$, $R_4$ and $X_a$ are defined herein. The compounds of the invention are useful for treating diseases and pathological conditions involving inflammation, immunological disorders and allergic disorders. Also disclosed are processes for preparing these compounds and to pharmaceutical compositions comprising these compounds.

15 Claims, No Drawings

OTHER PUBLICATIONS

Fang, J. et al; 2–Aminobenzimidazoles as Neuropeptide Y Y5 Antagonists: Solution Phase Synthesis and Structure Relationships, ACS National Meeting, Chicago, IL, Aug. 26, 2001.

Linn, J., et al; Benzimidazole Neuropeptide Y Y5 Antagonists: Rapid SAR Development Using a Solid–Phase Approach, ACS National Meeting, Chicago, IL, Aug. 26, 2001.

Heyer, D. et al; Discovery of a Novel Series of Benzimidazole–based Neuropeptide Y Y5 Antagonists from a 7–TM Targeted Chemical Library, ACS National Meeting, Chicago, IL Aug. 26, 2001.

Akwabi–Ameyaw, A. et al; Synthesis and SAR of Substituted 5 Acylamino Benzimidazoles as Potent Neuropeptide Y Y5 Antagonist,–ACS National Meeting, Chicago, IL, Aug. 26, 2001.

Kong, D.Y., et al; Chemial Components of Viscum Coloratum; Chinese Journal of Pharmaceuticals, 1989, 20(3) pp. 110–115.

Abstracts—American Chemical Society—Division of Medicinal Chemistry—222nd ACS National Meeting, Chicago, IL—Aug. 26–30, 2001.

* cited by examiner

SUBSTITUTED BENZIMIDAZOLE COMPOUNDS

APPLICATION DATA

This application claims benefit to U.S. provisional application No. 60/344,636 filed Nov. 9, 2001.

TECHNICAL FIELD OF THE INVENTION

This invention relates to substituted benzimidazole compounds of formula (I):

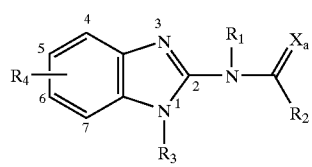

wherein $R_1$, $R_2$, $R_3$, $R_4$ and $X_a$ are defined herein below. The compounds of the invention are useful as inhibitors of the Tec kinase family, including Itk kinase, and are therefore useful for treating diseases and pathological conditions involving inflammation, immunological disorders and allergic disorders. This invention also relates to processes for preparing these compounds and to pharmaceutical compositions comprising these compounds.

BACKGROUND OF THE INVENTION

Protein kinases play a critical role in mediating signaling events leading to cellular responses such as activation, growth and differentiation, in response to extracellular signals. Protein kinases transmit their signal by phosphorylating specific residues in a target protein. Protein kinases that specifically phosphorylate tyrosine residues are referred to as protein tyrosine kinases. Protein tyrosine kinases can be divided into two general groups: receptor such as epidermal growth factor (EGF) receptor (S. Iwashita and M. Kobayashi, 1992, Cellular Signalling, 4, 123–132) and cytosolic non-receptor (C. Chan et al., 1994, Ann. Rev. Immunol., 12, 555–592).

Interleukin-2-inducible T cell kinase (Itk), also referred to as T cell-specific kinase (Tsk) and expressed mainly in T-lymphocytes (EMT), is a member of the Tec family of protein tyrosine kinases that also includes Txk, Tec, Btk, and Bmx. Tec family members are characterized by the presence of a pleckstrin-homology domain (PH), a proline rich Tec homology domain (TH) and Src homology SH3, SH2 and SH1 kinase domains positioned from the N-terminus to the C-terminus respectively (S. Gibson et al., 1993, Blood, 82,1561–1572; J. D. Siliciano et al., 1992, Proc. Nat. Acad. Sci., 89, 11194–11198; N. Yamada et al., 1993 Biochem. and Biophys Res. Comm., 192, 231–240).

Itk is expressed in T cells, mast cells and natural killer cells. It is activated in T cells upon stimulation of the T cell receptor (TCR), and in mast cells upon activation of the high affinity IgE receptor. Following receptor stimulation in T cells, Lck, a src tyrosine kinase family member, phosphorylates Y511 in the kinase domain activation loop of Itk (S. D. Heyeck et al., 1997, J. Biol. Chem, 272, 25401–25408). Activated Itk, together with Zap-70 is required for phosphorylation and activation of PLC-γ (S. C. Bunnell et al., 2000, J. Biol. Chem., 275, 2219–2230). PLC-γ catalyzes the formation of inositol 1,4,5-triphosphate and diacylglycerol, leading to calcium mobilization and PKC activation, respectively. These events activate numerous downstream pathways and lead ultimately to degranulation (mast cells) and cytokine gene expression (T cells) (Y. Kawakami et al., 1999, J. Leukocyte Biol., 65, 286–290).

The role of Itk in T cell activation has been confirmed in Itk knockout mice. CD4+T cells from Itk knockout mice have a diminished proliferative response in a mixed lymphocyte reaction or upon Con A or anti-CD3 stimulation. (X. C. Liao and D. R. Littman, 1995, Immunity, 3, 757–769). Also, T cells from Itk knockout mice produced little IL-2 upon TCR stimulation resulting in reduced proliferation of these cells. In another study, Itk deficient CD4+ T cells produced reduced levels of cytokines including IL-4, IL-5 and IL-13 upon stimulation of the TCR, even after priming with inducing conditions. (D. J. Fowell, 1999, Immunity, 11, 399–409).

The role of Itk in PLC-γ activation and in calcium mobilization was also confirmed in the T cells of these knockout mice, which had severely impaired $IP_3$ generation and no extracellular calcium influx upon TCR stimulation (K. Liu et al., 1998, J. Exp. Med. 187, 1721–1727). The studies described above support a key role for Itk in activation of T cells and mast cells. Thus an inhibitor of Itk would be of therapeutic benefit in diseases mediated by inappropriate activation of these cells.

It has been well established that T cells play an important role in regulating the immune response (Powrie and Coffman, 1993, Immunology Today, 14, 270–274). Indeed, activation of T cells is often the initiating event in immunological disorders. Following activation of the TCR, there is an influx of calcium that is required for T cell activation. Upon activation, T cells produce cytokines, including IL-2, 4, 5, 9, 10, and 13 leading to T cell proliferation, differentiation, and effector function. Clinical studies with inhibitors of IL-2 have shown that interference with T cell activation and proliferation effectively suppresses immune response in vivo (Waldmann, 1993, Immunology Today, 14, 264–270). Accordingly, agents that inhibit T lymphocyte activation and subsequent cytokine production, are therapeutically useful for selectively suppressing the immune response in a patient in need of such immunosuppression.

Mast cells play a critical roll in asthma and allergic disorders by releasing pro-inflammatory mediators and cytokines. Antigen-mediated aggregation of FcεRI, the high-affinity receptor for IgE results in activation of mast cells (D. B. Corry et al., 1999, Nature, 402, B18–23). This triggers a series of signaling events resulting in the release of mediators, including histamine, proteases, leukotrienes and cytokines (J. R. Gordon et al., 1990, Immunology Today, 11, 458–464.) These mediators cause increased vascular permeability, mucus production, bronchoconstriction, tissue degradation and inflammation thus playing key roles in the etiology and symptoms of asthma and allergic disorders.

Recent published data using Itk knockout mice suggests that in the absence of Itk function, increased numbers of memory T cells are generated (A. T. Miller et al., 2002 The Journal of Immunology, 168, 2163–2172). One strategy to improve vaccination methods is to increase the number of memory T cells generated (S. M. Kaech et al., Nature Reviews Immunology, 2, 251–262).

All documents cited in this application are incorporated by reference in their entirety.

SUMMARY OF THE INVENTION

It is therefore an object of the invention to provide a compound of the formula (I):

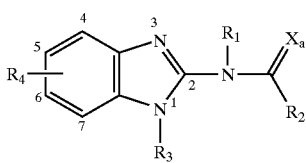

wherein $R_1$, $R_2$, $R_3$, $R_4$ and $X_a$ are defined herein below.

It is another object of the invention to provide a method of inhibiting the Tec kinase family, including Itk kinase, and methods of treating diseases or conditions related to such kinase activity, by administering to a patient in need thereof a therapeutically effective amount of a compound of the formula (I).

It is yet another object of the invention to provide pharmaceutical compositions and processes of making compounds of the formula (I) as described herein below.

DETAILED DESCRIPTION OF THE PREFERRED EMBODIMENTS

In it's broadest generic embodiment, the invention provides for a compound of the formula (I):

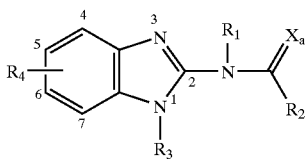

wherein:

$R_1$ is hydrogen or alkyl;
$R_2$ is chosen from aryl and heteroaryl each $R_2$ is optionally substituted with one or more $R_a$;
$R_3$ is $C_{1-10}$ alkyl chain branched or unbranched optionally substituted with one or more $R_b$,
or $R_3$ is the group:
—$(CH_2)_n$-L-$R_6$, wherein L is chosen from a bond, —NH—C(O)—, —O—C(O)—, —C(O)— and —S(O)$_m$— wherein m is 0, 1 or 2, and wherein said group is optionally substituted by one or more $R_b$;
wherein $R_6$ is independently chosen from hydroxy, alkyl, alkoxy, alkylthio, aryl$C_{0-5}$ alkyl, aryloxy$C_{0-5}$ alkyl, heteroaryl$C_{0-5}$ alkyl, cycloalkyl$C_{0-5}$ alkyl, heterocyclyl$C_{0-5}$ alkyl and amino said amino is optionally mono-or di-substituted by acyl, alkyl, alkoxycarbonyl, cycloalkyl$C_{0-5}$ alkyl, aryl$C_{0-5}$ alkyl, heteroaryl$C_{0-5}$ alkyl or heterocyclyl$C_{0-5}$ alkyl;
n is 1–10;
$R_4$ is the group:

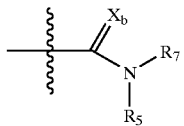

wherein $R_4$ is covalently attached at the indicated 5- or 6-position of the formula (I);
$R_5$ is chosen from aryl$C_{0-5}$ alkyl, alkyl, heteroaryl$C_{0-5}$ alkyl, cycloalkyl$C_{0-5}$ alkyl and heterocyclyl$C_{0-5}$ alkyl, each $R_5$ optionally substituted with one or more $R_c$;

$R_7$ is hydrogen, alkenyl or alkyl;
or $R_5$ and $R_7$ together with the nitrogen atom to which they are attached form:
a 4–7-membered monocyclic ring or
an 8–14-membered bicyclic ring,
wherein each monocyclic or bicyclic ring optionally contains an additional 1 to 3 heteroatoms chosen from N, O and S and each ring is aromatic or nonaromatic, and wherein each monocyclic or bicyclic ring is optionally substituted by one or more $R_c$;
each $R_a$, $R_b$ or $R_c$ are independently chosen from hydrogen, alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono- or -di-substituted by alkyl, acyl or alkoxycarbonyl, wherein any of the above $R_a$, $R_b$ or $R_c$ are optionally halogenated where possible; and
$X_a$ and $X_b$ are oxygen or sulfur;
or the pharmaceutically acceptable derivatives thereof.

In another embodiment, there is provided a compound of the formula (I) as described immediately above and wherein:

$R_1$ is hydrogen;
$R_2$ is chosen from phenyl, naphthyl, and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl each $R_2$ is optionally substituted with one or more $R_a$;
$R_3$ is $C_{1-10}$ alkyl chain branched or unbranched optionally substituted with one or more $R_b$,
or $R_3$ is:
—$(CH_2)_n$-L-$R_6$, wherein L is chosen from a bond, —O—C(O)—, —C(O)— and —S(O)$_m$— wherein m is 0, 1 or 2, and wherein said group is optionally substituted by one or more $R_b$;
wherein $R_6$ is independently chosen from hydroxy, $C_{1-5}$ alkyl, $C_{1-5}$ alkoxy, $C_{1-5}$ alkylthio, phenyl, naphthyl, benzyl, phenethyl, heteroaryl$C_{0-5}$ alkyl, $C_{3-7}$ cycloalkyl$C_{0-5}$ alkyl, heterocyclyl$C_{0-5}$ alkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl, heteroaryl$C_{0-5}$ alkyl or heterocyclyl$C_{0-5}$ alkyl; and wherein each recited heteroaryl in this paragraph is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl and wherein each recited heterocyclyl in this paragraph is chosen from pyrrolidinyl, morpholinyl, thiomorpholinyl, dioxalanyl, piperidinyl and piperazinyl;
$R_5$ is chosen from phenyl, naphthyl, benzyl, phenethyl, $C_{1-5}$ alkyl, heteroaryl$C_{0-5}$ alkyl wherein the heteroaryl is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl, $C_{3-7}$ cycloalkyl$C_{0-5}$ alkyl and heterocyclyl$C_{0-5}$ alkyl wherein the heterocyclyl is chosen from aziridinyl, pyrrolidinyl, morpholinyl, thiomorpholinyl, tetrahydrofuranyl, dioxalanyl, piperidinyl and piperazinyl, each $R_5$ is optionally substituted with one or more $R_c$;
each $R_a$, $R_b$ or $R_c$ are independently chosen from hydrogen, $C_{1-5}$ alkyl, $C_{2-5}$ alkenyl, $C_{2-5}$ alkynyl, $C_{3-8}$ cycloalkyl, phenyl, benzyl, phenoxy, $C_{1-5}$ alkoxy, $C_{1-5}$ alkylthio, $C_{1-5}$ acyl, $C_{1-5}$ alkoxycarbonyl, $C_{1-5}$ acyloxy, $C_{1-5}$ acylamino, $C_{1-5}$ sulphonylamino, aminosulfonyl, $C_{1-5}$ alkylsulfonyl, carboxy, carboxamide, hydroxy, halogen, trifluoromethyl, nitro, nitrile and amino optionally mono- or -di-substituted by $C_{1-5}$ alkyl, $C_{1-5}$ acyl or $C_{1-5}$ alkoxycarbonyl, wherein any of the above $R_a$, $R_b$ or $R_c$ are optionally halogenated where possible;
$R_7$ is $C_{3-10}$ alkenyl or $C_{1-5}$ alkyl; and
$X_a$ and $X_b$ are oxygen.

In yet another embodiment, there is provided a compound of the formula (I) as described immediately above and wherein:

$R_2$ is chosen from phenyl, naphthyl and heteroaryl chosen from thienyl, furanyl, isoxazolyl, oxazolyl, imidazolyl, thiadiazolyl, pyrazolyl, pyridinyl, quinoxalinyl and benzothienyl each $R_2$ is optionally substituted with one or more $R_a$;
$R_6$ is independently chosen from hydroxy, $C_{1-5}$ alkyl, $C_{1-5}$ alkoxy, phenyl, benzyl, phenethyl, heteroaryl$C_{0-5}$ alkyl, heterocyclyl$C_{0-5}$ alkyl, $C_{3-7}$ cycloalkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl or heteroaryl$C_{0-5}$ alkyl;
and wherein each recited heteroaryl in this paragraph is chosen from thienyl, furanyl, isoxazolyl, oxazolyl, thiazolyl, thiadiazolyl, tetrazolyl, pyrazolyl, pyrrolyl and imidazolyl;
n is 1–6;
$R_5$ is chosen from phenyl, naphthyl, benzyl, phenethyl, $C_{1-5}$ alkyl, heteroaryl$C_{0-5}$ alkyl wherein the heteroaryl in this paragraph is chosen from thienyl, furanyl, imidazolyl and pyridinyl, $C_{3-7}$ cycloalkyl$C_{0-5}$ alkyl and heterocyclyl$C_{0-5}$ alkyl wherein the heterocyclyl is chosen from aziridinyl, pyrrolidinyl, tetrahydrofuranyl, tetrahydropyridinyl, morpholinyl, thiomorpholinyl, piperidinyl and piperazinyl, each $R_5$ is optionally substituted with one or more $R_c$; and
and $R_7$ is propenyl or $C_{1-3}$ alkyl.

In yet still another embodiment, there is provided a compound of the formula (I) as described immediately above and wherein:

$R_2$ is chosen from phenyl and heteroaryl chosen from thienyl, furanyl, isoxazolyl, thiadiazolyl, pyrazolyl and pyridinyl each $R_2$ is optionally substituted with one or more $R_a$;
$R_3$ is:
—$(CH_2)_n$—$C(O)$—$R_6$ or
—$(CH_2)_n$—$R_6$;
wherein $R_6$ is independently chosen from hydroxy, $C_{1-5}$ alkyl, $C_{1-5}$ alkoxy, phenyl, thienyl$C_{0-5}$ alkyl, $C_{3-7}$ cycloalkyl and amino said amino is optionally mono- or di-substituted by $C_{1-5}$ alkyl or $C_{1-5}$ alkoxycarbonyl;
$R_5$ is chosen from phenyl, benzyl, phenethyl and $C_{3-7}$ cycloalkyl$C_{0-5}$ alkyl each optionally substituted with one or more $R_c$;
each $R_a$, $R_b$ or $R_c$ are independently chosen from $C_{1-5}$ alkyl, $C_{3-8}$ cycloalkyl, phenyl, $C_{1-5}$ alkoxy, amino optionally mono- or -di-substituted by $C_{1-5}$ alkyl, $C_{1-5}$ alkoxycarbonyl, carboxamide, hydroxy, halogen, trifluoromethyl, nitro and nitrile, wherein any of the above $R_a$, $R_b$ or $R_c$ are optionally halogenated where possible;
and $R_7$ is $C_{1-3}$ alkyl.

In a further embodiment, there is provided a compound of the formula (I) as described immediately above and wherein:

$R_2$ is chosen from phenyl, thienyl, furanyl, isoxazolyl and pyridinyl each optionally substituted with one or more $R_a$;
$R_5$ is chosen from phenyl and cyclohexyl each optionally substituted with one or more $R_c$; and
n is 2–5.

In yet another embodiment, there is provided a compound of the formula (I) as described immediately above and wherein:

$R_2$ is chosen from phenyl, thien-2-yl, isoxazol-5-yl and pyridin-3-yl each optionally substituted with one or more $R_a$;
$R_6$ is independently chosen from hydroxy, methyl, ethyl, $C_{1-3}$ alkoxy, phenyl, thienyl$C_{0-5}$ alkyl, $C_{3-7}$ cycloalkyl and amino said amino is optionally mono- or di-substituted by $C_{1-5}$ alkyl or $C_{1-5}$ alkoxycarbonyl; and
each $R_a$, $R_b$ or $R_c$ are independently chosen from $C_{1-3}$ alkoxy, amino optionally mono- or -di-substituted by $C_{1-3}$ alkyl, carboxamide, hydroxy, fluoro, chloro, bromo, trifluoromethyl, nitro and nitrile.

In any of the aforementioned embodiments, there are provided compounds of the formula (I) wherein:

$R_4$ is covalently attached at the indicated 5-position of the formula (I) or in another embodiment $R_4$ is covalently attached at the indicated 6-position of the formula (I).

In another embodiment there is provided representative compounds of the invention which can be made in accordance with the general schemes and working examples presented below:

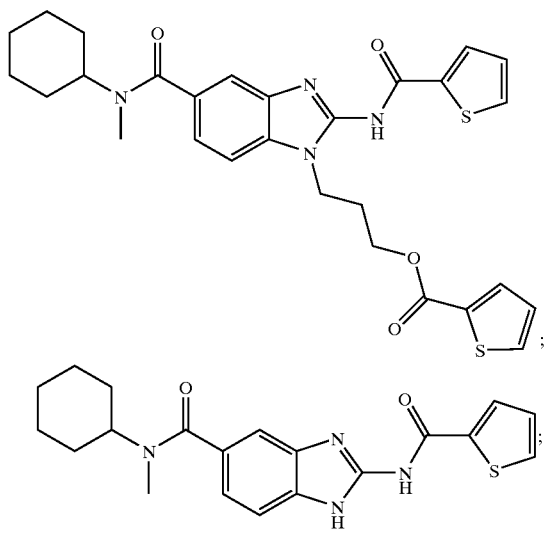

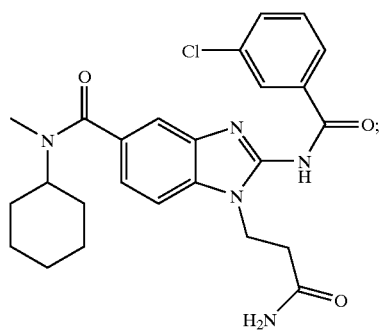
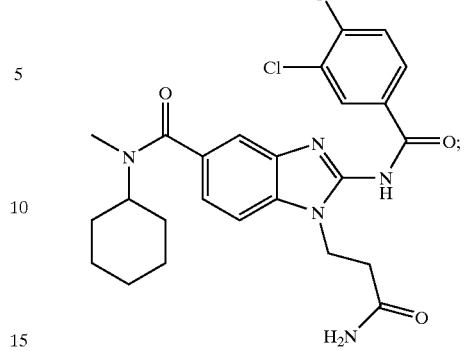
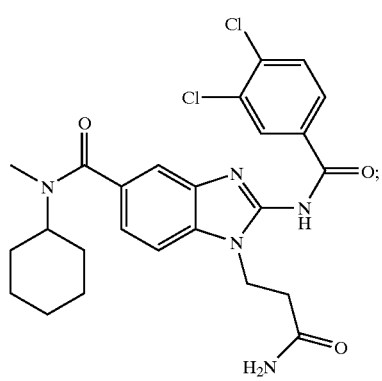
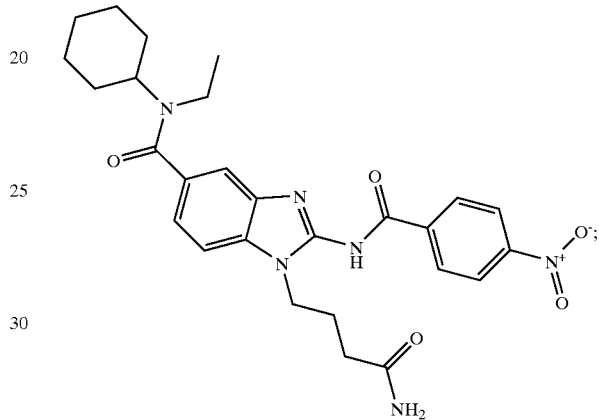
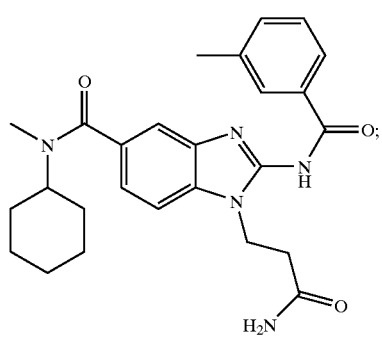
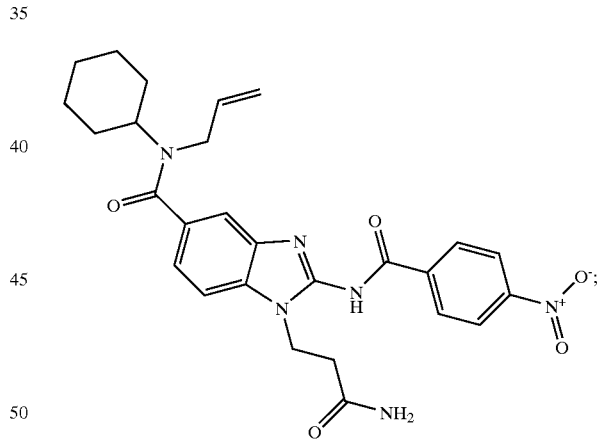
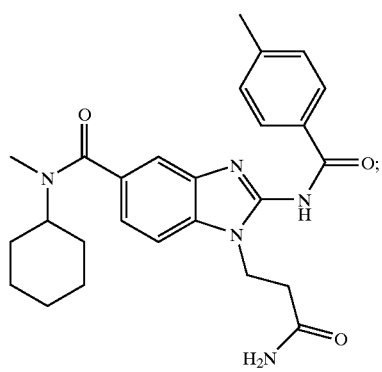
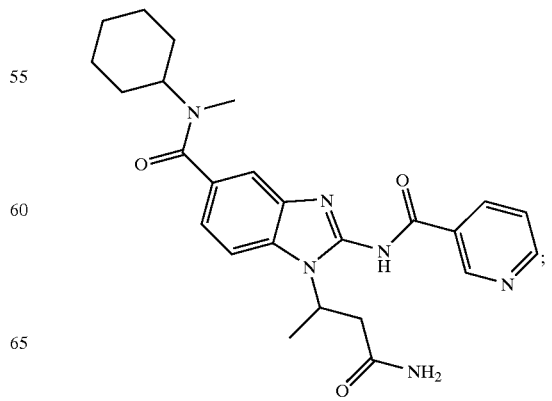

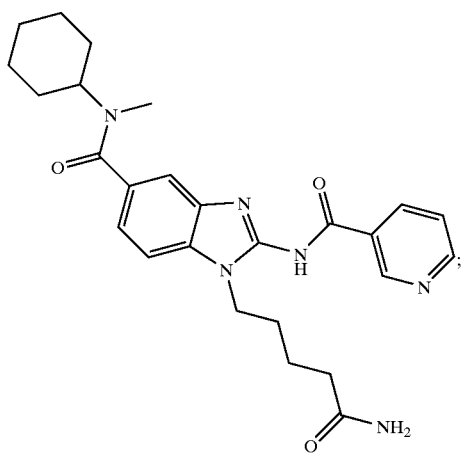
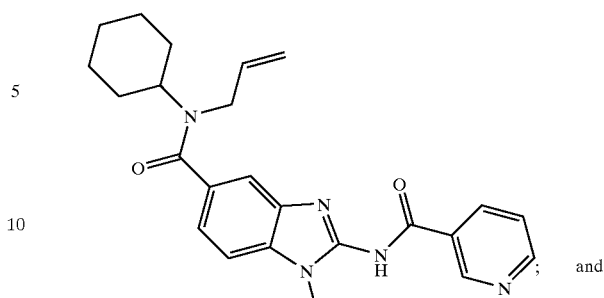
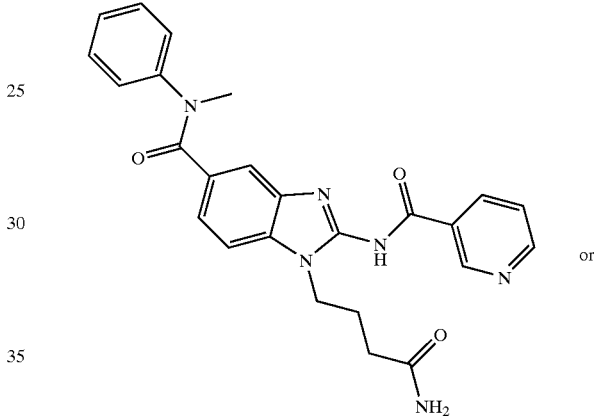
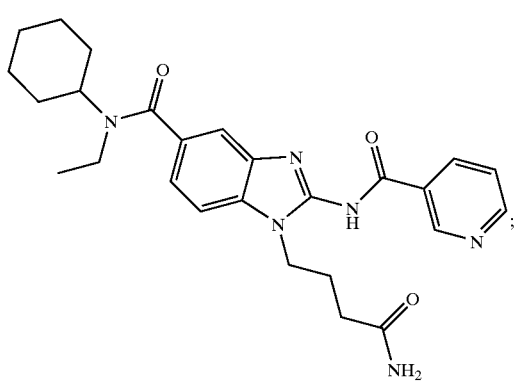
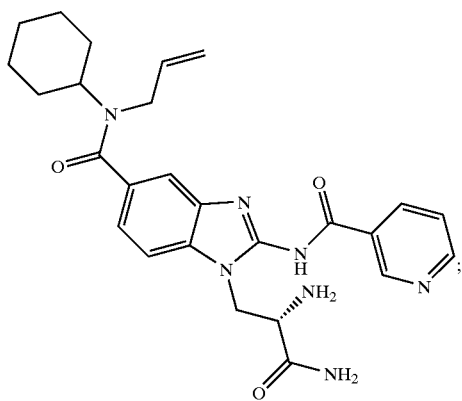
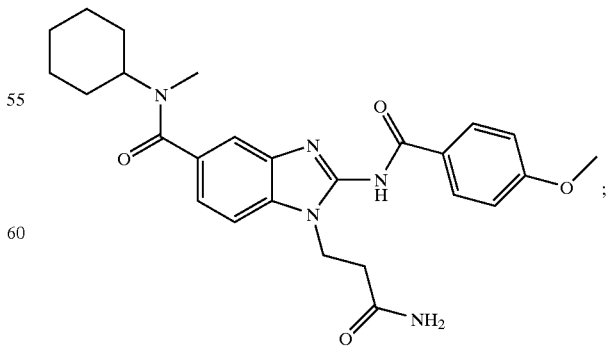
the pharmaceutically acceptable derivatives thereof.
In another embodiment there is provided representative compounds of the invention which are preferred and can be made in accordance with the general schemes and working examples presented below:

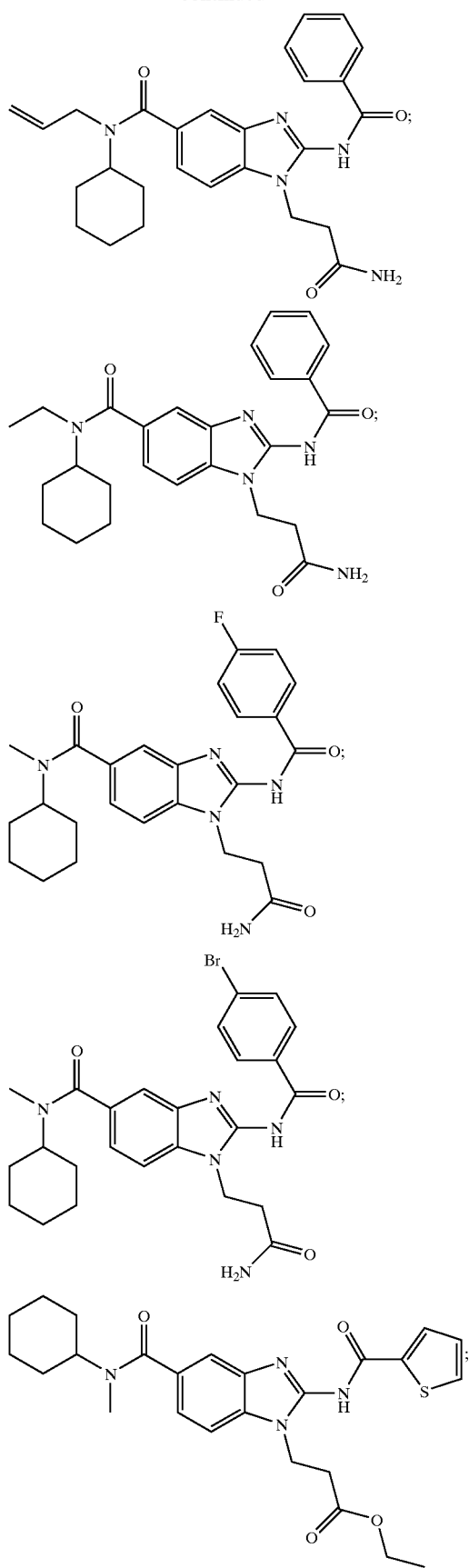
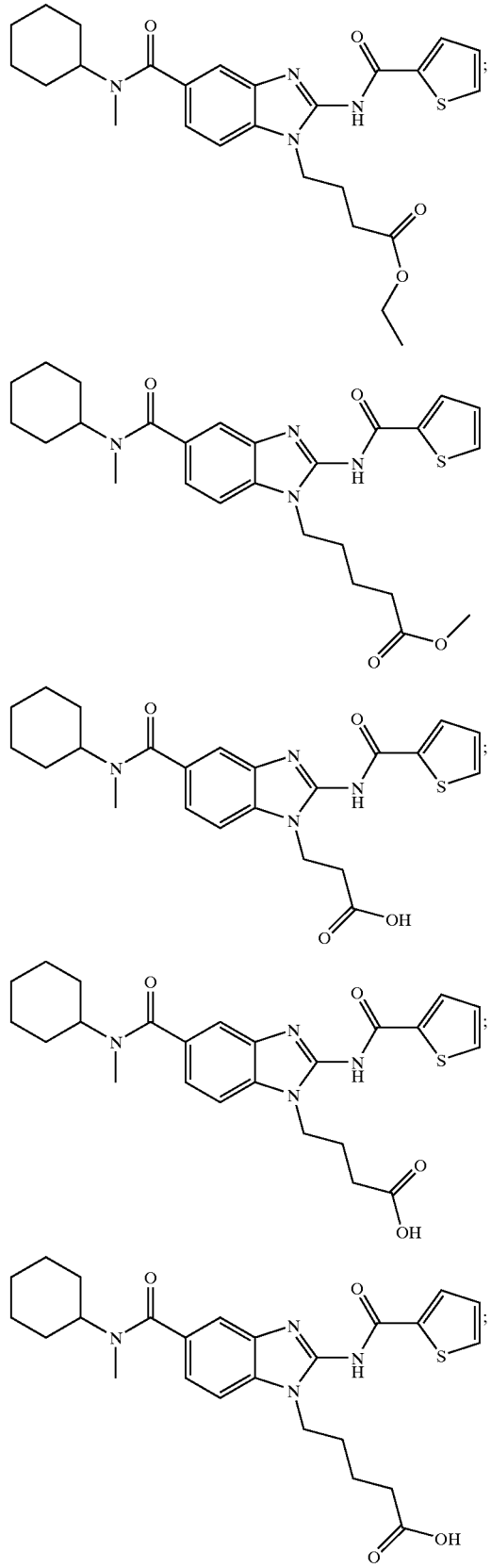

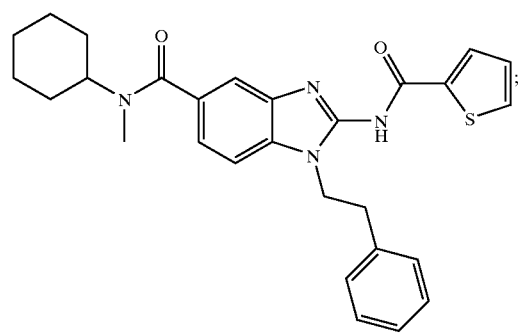
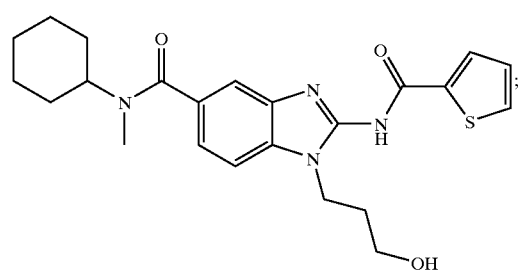
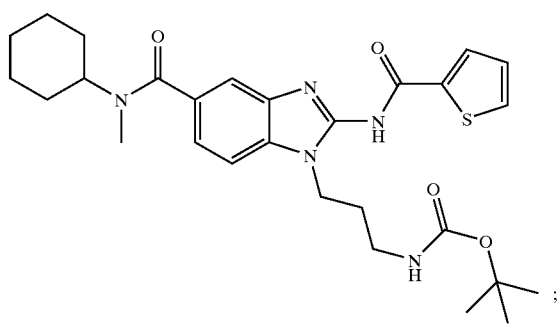
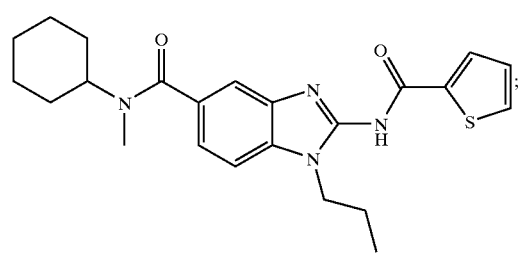
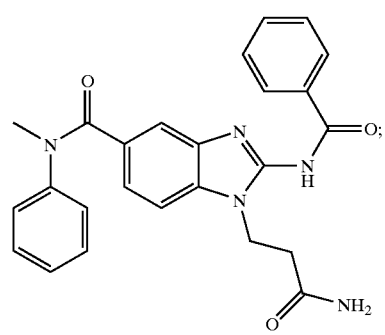
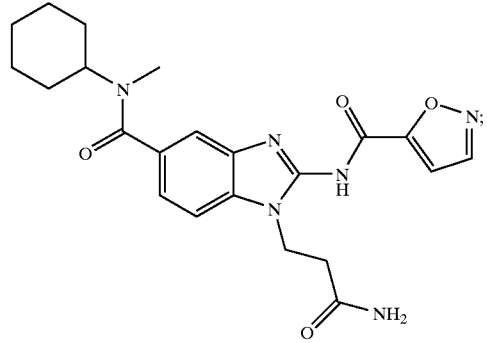
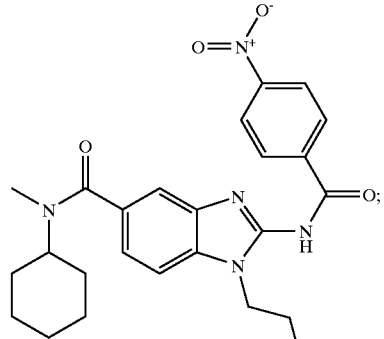
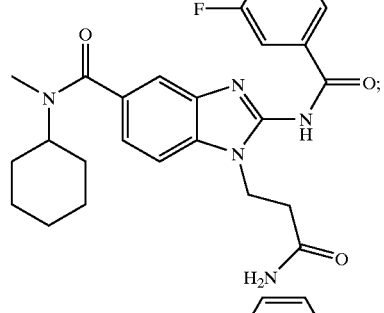
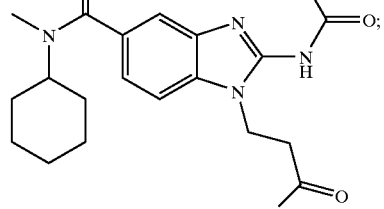
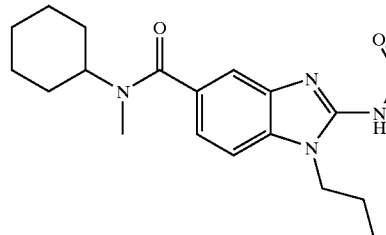

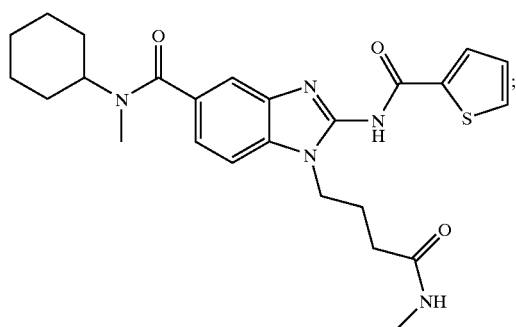
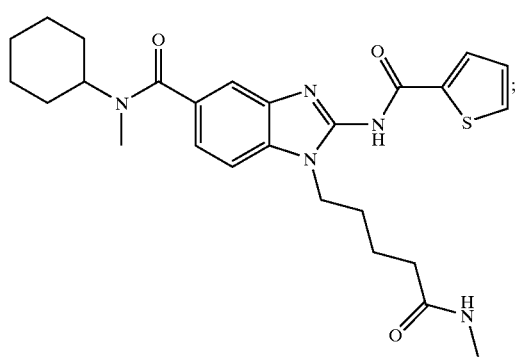
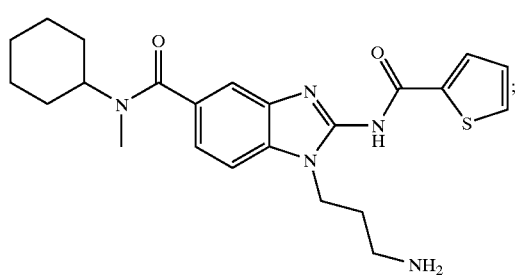
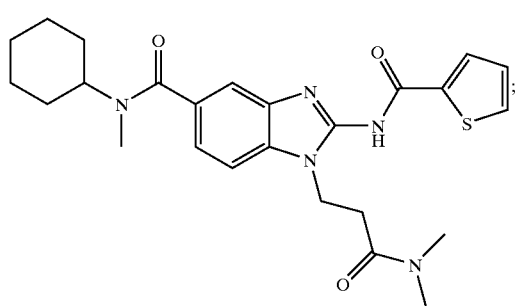
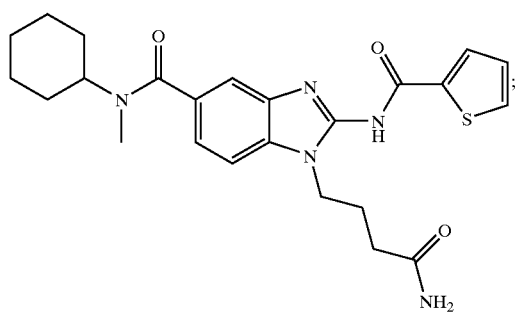
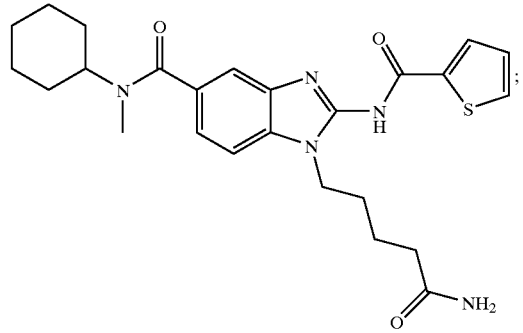
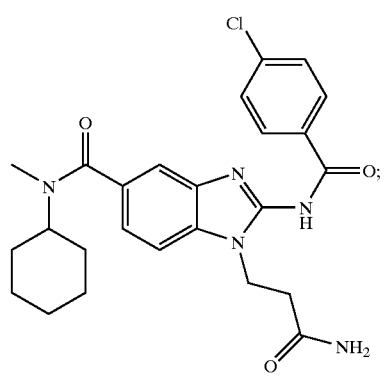
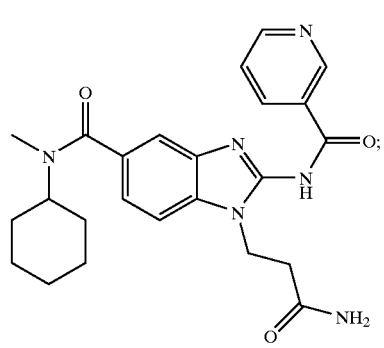
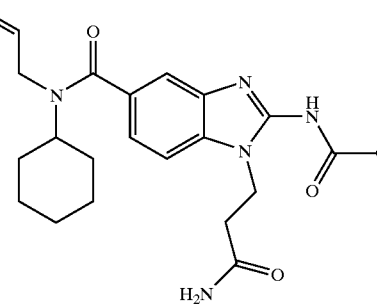
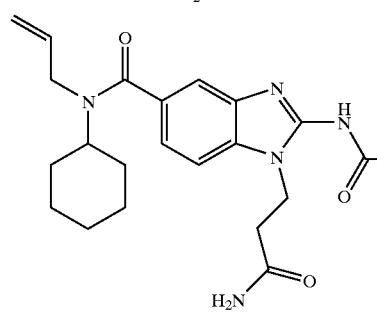

-continued
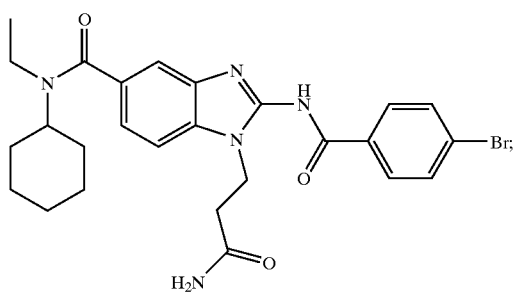
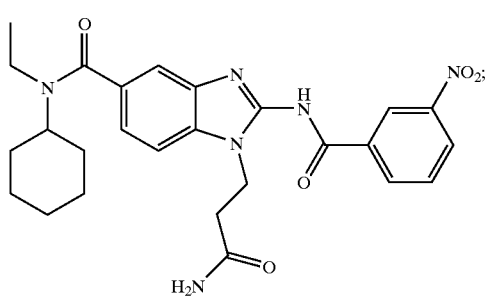
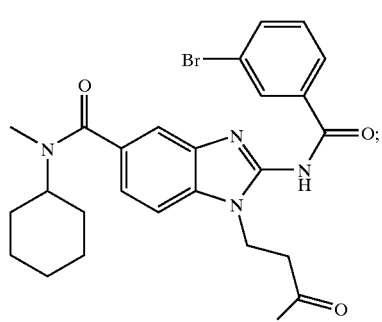
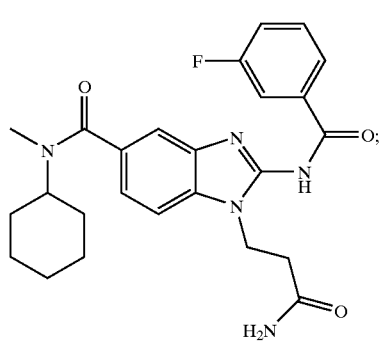
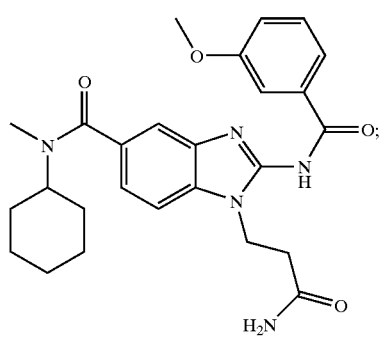
-continued
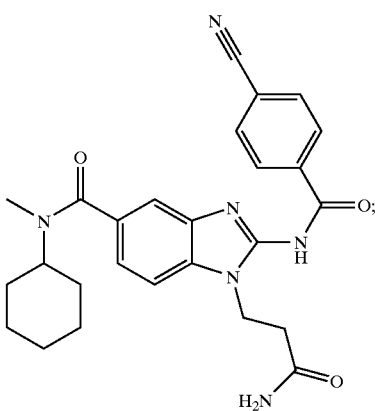
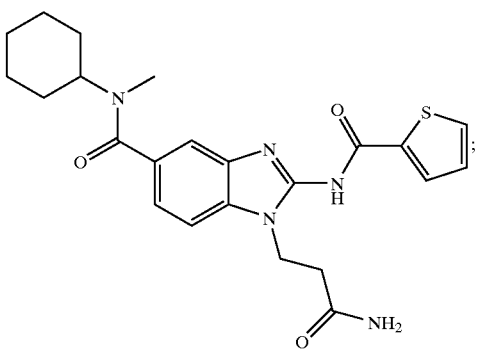
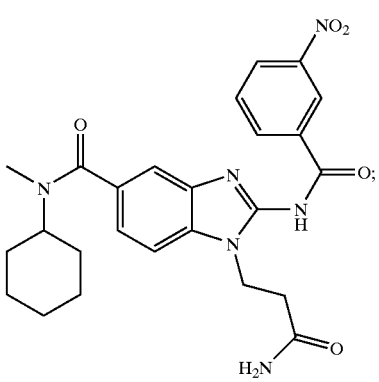
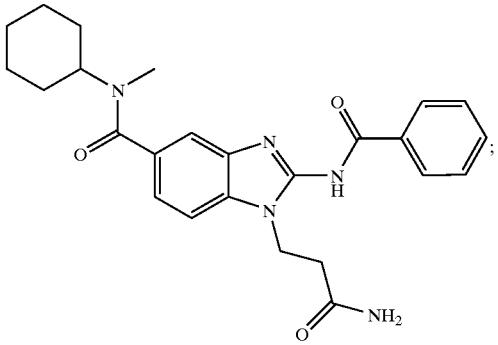

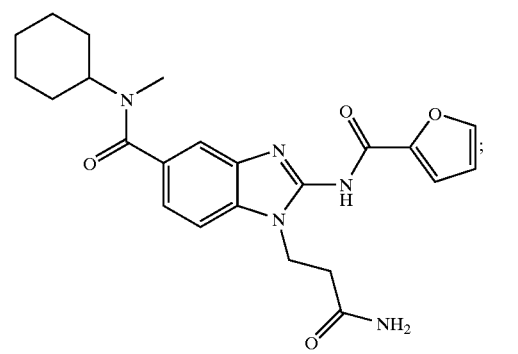
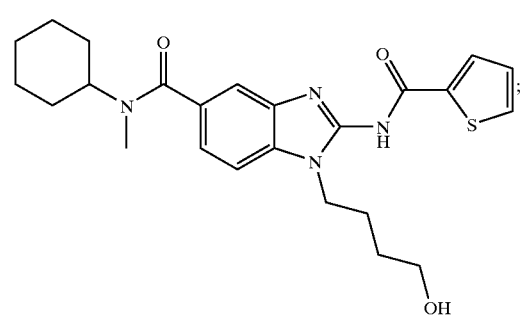
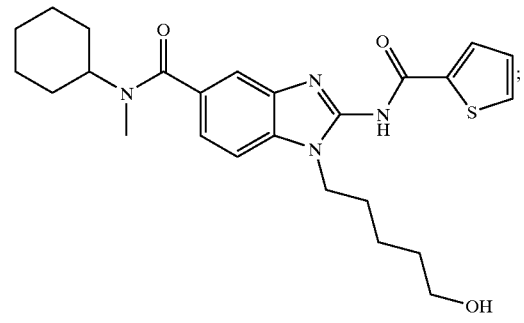
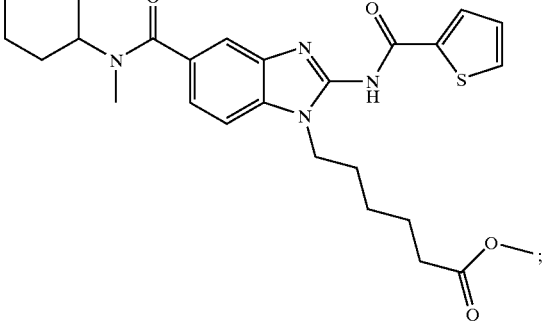
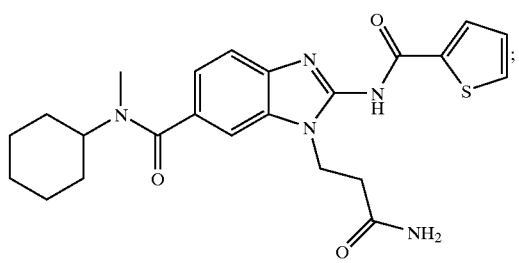
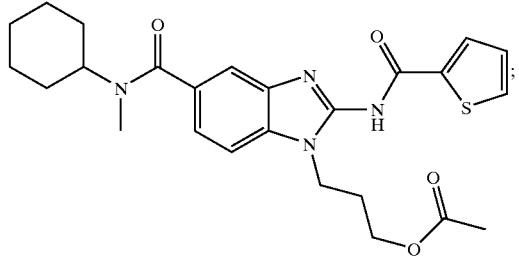
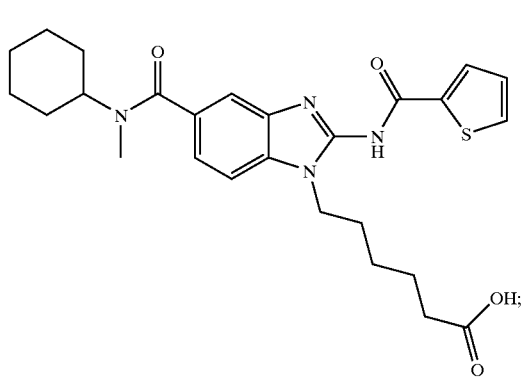
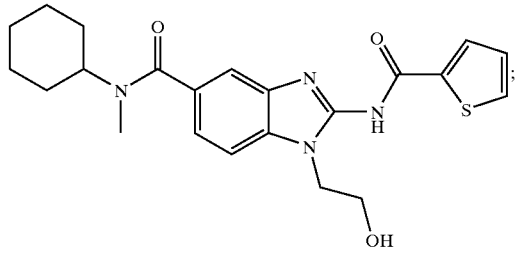
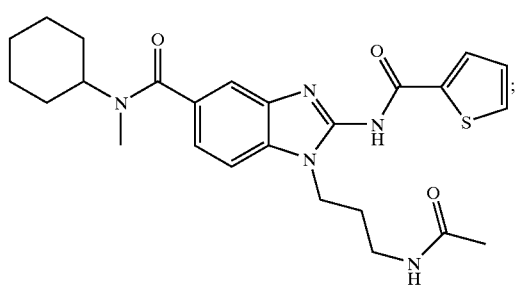

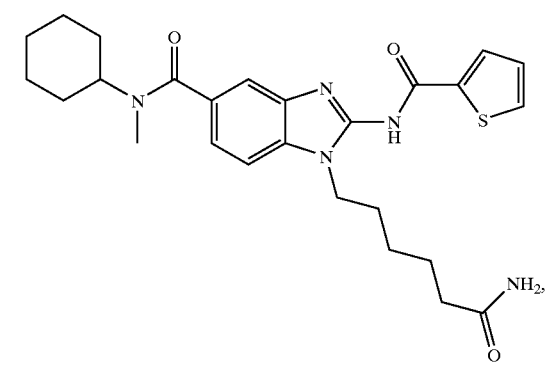
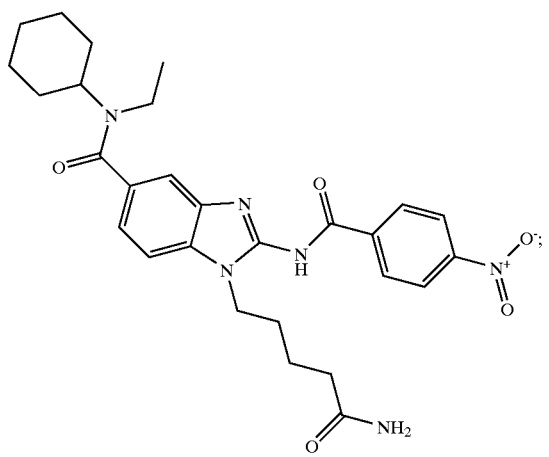
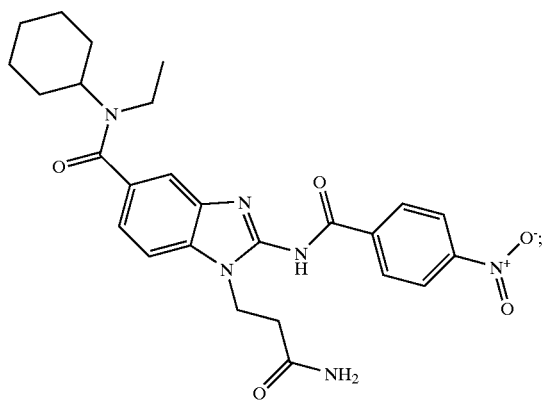
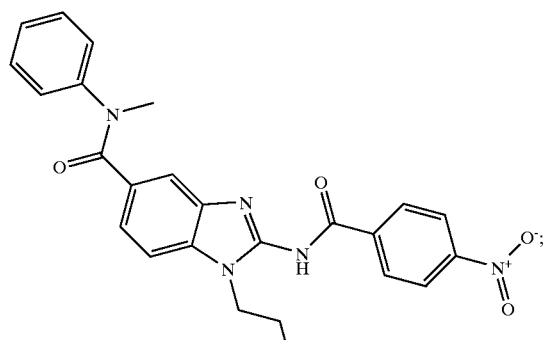
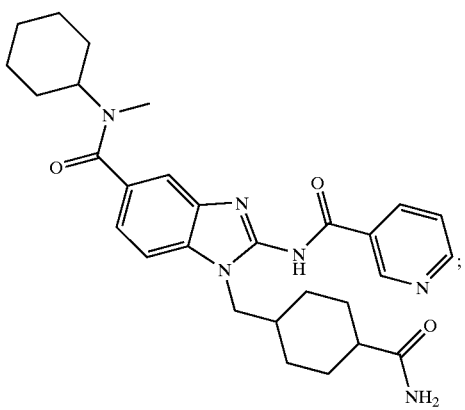
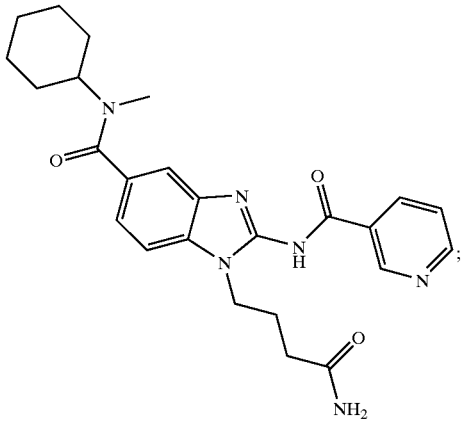
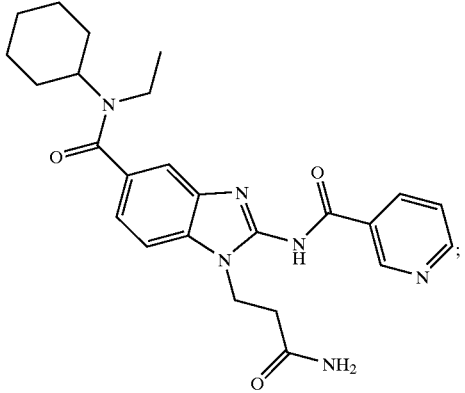

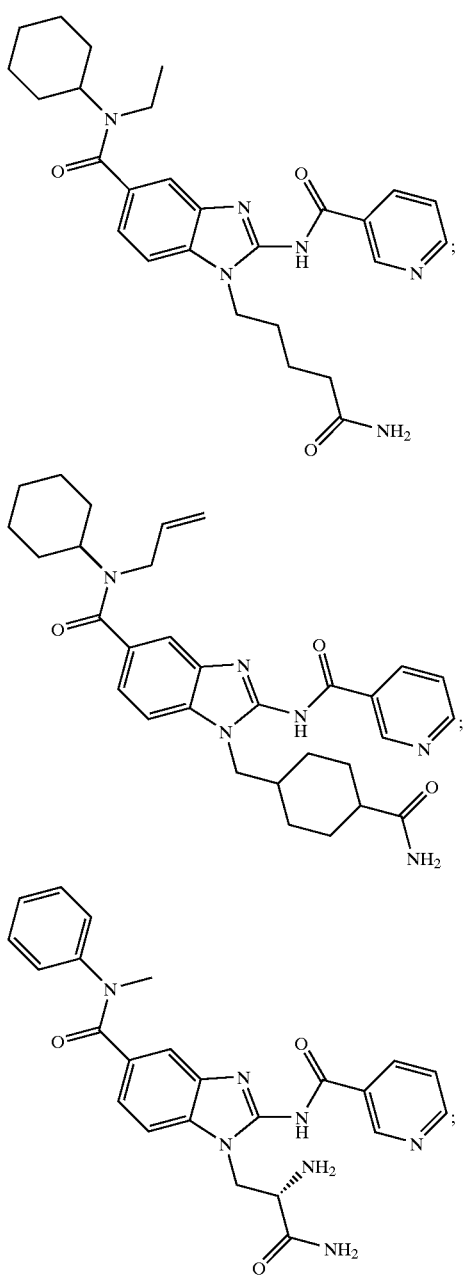

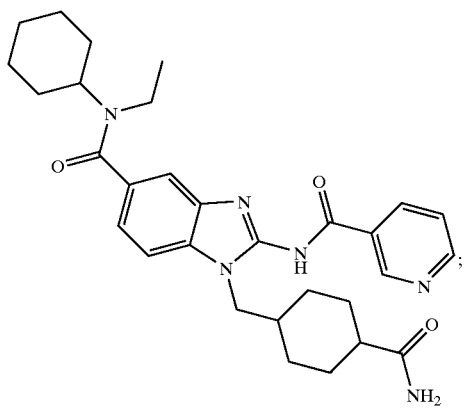

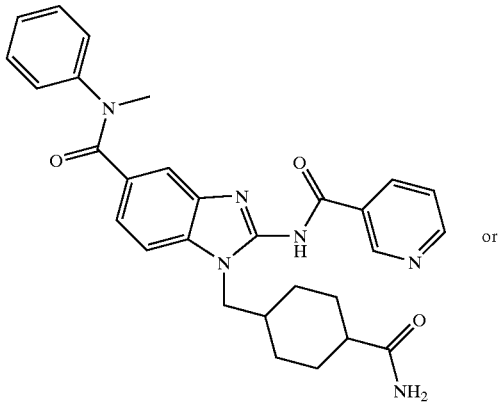

the pharmaceutically acceptable derivatives thereof.

In all the compounds disclosed herein above in this application, in the event the nomenclature is in conflict with the structure, it shall be understood that the compound is defined by the structure.

The invention includes the use of any compounds described above containing one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. For example, other tautomers will be apparent to those of ordinary skill in the art, the invention includes all such tautomers and methods of making and using the same.

All terms as used herein in this specification, unless otherwise stated, shall be understood in their ordinary meaning as known in the art.

Alkyl, alkenyl, alkynyl, alkoxy, alkylthio, acyl, alkoxycarbonyl, acyloxy, acylamino, alkylsulfonyl and all other alkyl containing groups shall be understood unless otherwise specified as being C1–10, branched or unbranched where structurally possible, and optionally partially or fully halogenated. Other more specific definitions are as follows:

BOC or t-BOC is tertiary-butoxycarbonyl.
t-Bu is tertiary-butyl.
DMF is dimethylformamide.
EtOAc is ethyl acetate.
EtOH and MeOH are ethanol and methanol, respectively.
TFA is trifluoroacetic acid.
THF is tetrahydrofuran.
DMSO is dimethylsulfoxide.
TBTU is O-(1H-benzotriazol-1-yl)-N,N,N',N'-tetramethyluronium tetrafluoroborate.
FMOC is 9-fluorenylmethoxycarbonyl.

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems, and optionally or fully halogenated. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, pyrrolidinyl, morpholinyl, thiomorpholinyl, dioxalanyl, piperidinyl, piperazinyl, aziridinyl and tetrahydrofuranyl.

The term "heteroaryl" shall be understood to mean an aromatic 5–8 membered monocyclic or 8–11 membered bicyclic ring containing 1–4 heteroatoms such as N, O and S. Unless otherwise stated, such heteroaryls include but are not limited to thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl.

The term "heteroatom" as used herein shall be understood to mean atoms other than carbon such as O, N, S and P.

In all alkyl groups or carbon chains within cycloalkyl groups, where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain.

Substitution on a carbon such as a methylene carbon by groups such as oxo result in definitions such as: alkoxycarbonyl, acyl, and amido, or if substituted on a ring can, for example, replace a methylene group —CH$_2$— with a carbonyl >C=O.

The term "aryl" as used herein shall be understood to mean aromatic carbocycle or heteroaryl as defined herein. Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydranaphthyl. Each may be partially or fully halogenated. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective functional group.

As used herein, "nitrogen" and "sulfur" include any oxidized form of nitrogen and sulfur and the quaternized form of any basic nitrogen. For example, for an alkylthio radical such as —S—C$_{1-6}$ alkyl, unless otherwise specified, this shall be understood to include —S(O)—C$_{1-6}$ alkyl and —S(O)$_2$—C$_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. A non-limiting example would be a halogenated alkyl such as —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The term "patient" refers to a warm-blooded mammal and preferably, a human.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$–C$_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed herein above, thereby imparting the desired pharmacological effect.

METHODS OF THERAPEUTIC USE

The compounds of the invention are effective inhibitors of Tec kinase family activity, especially of Itk. Therefore, in one embodiment of the invention, there is provided methods of treating immunological disorders using compounds of the invention. In another embodiment, there is provided methods of treating inflammatory disorders using compounds of the invention. In yet another embodiment, there is provided methods of treating allergic disorders using compounds of the invention. In yet still another embodiment, there is provided methods of enhancing memory cell generation for vaccines using compounds of the invention. In a further embodiment, there is provided methods of treating cell proliferative disorders using compounds of the invention.

Without wishing to be bound by theory, the compounds of this invention modulate T cell and mast cell activation via effective inhibition of Itk. The inhibition of T cell activation is therapeutically useful for selectively suppressing immune function. Thus, the inhibition of Itk is an attractive means for preventing and treating a variety of immune disorders, including inflammatory diseases, autoimmune diseases, organ and bone marrow transplant rejection and other disorders associated with T cell mediated immune response. In particular, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, cancer, graft versus host disease (and other forms of organ or bone marrow transplant rejection) and lupus erythematosus.

The compounds of the invention are also effective inhibitors of Tec family kinases other than Itk including Txk, Tec, Btk, and Bmx and would thus be useful in treating diseases associated with the activity of one or more of these Tec family kinases.

Inhibitors of mast cell activation and degranulation block the release of allergic and pro-inflammatory mediators and cytokines. Thus inhibitors of Itk have potential utility in treating inflammatory and allergic disorders, including asthma, chronic obstructive pulmonary disease (COPD), adult respiratory distress syndrome (ARDS), bronchitis, conjunctivitis, dermatitis and allergic rhinitis. Other disorders associated with T cell or mast cell mediated immune response will be evident to those of ordinary skill in the art and can also be treated with the compounds and compositions of this invention.

Inhibitors of Itk and other Tec family kinases have potential utility in combination with other therapies for the treatment of immune, inflammatory, proliferative, and allergic disorders. Examples, though not all encompassing, include co-administration with steroids, leukotriene antagonists, anti-histamines, cyclosporin, or rapamycin.

One strategy to improve vaccination methods is to increase the number of memory T cells generated. As described in the Background, in the absence of Itk in mice, increased numbers of memory cells are generated. Thus, within the scope of the invention is the use of the present compounds in the formulation of improved vaccines that generate increased numbers of memory T cells.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

BIOLOGICAL ACTIVITY

Itk Assay

Itk is purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly $Glu_4$: $Tyr_1$ (PGTYR). The screen utilizes the Zymark Allegro UHTS system to dispense reagents, buffers and samples for assay, and also to wash plates. The kinase assay is performed in kinase assay buffer (50 mM HEPES, pH 7.0, 25 mM $MgCl_2$, 5 mM $MnCl_2$, 50 mM KCl, 100 $\mu$M $Na_3VO_4$, 0.2% BSA, 0.01% CHAPS, 200 $\mu$M TCEP). Test samples initially dissolved in DMSO at 1 mg/mL, are pre-diluted for dose response (9 doses with starting final concentration of 3 $\mu$g/mL, 1 to 3 serial dilutions) with the assay buffer in 384-well polypropylene microtiter plates. A 10 $\mu$L volume/ well of a mixture of substrates containing 15 $\mu$M ATP and 9 ng/$\mu$L PGTYR-biotin (CIS Biointernational) in kinase buffer is added to neutravidin coated 384-well white plate (PIERCE), followed by 20 μL/well test sample solution and 20 μL/well of diluted enzyme (7 nM final conc.). Background wells are incubated with buffer, rather than 20 μL enzyme. The assay plates are incubated for 30 min at room temperature. Following incubation, the assay plates are washed three times with 100 μL wash buffer (50 mM Tris-HCL, pH 7.4, 150 mM NaCl, 0.05% Tween 20, 0.2% BSA). A 50 μL aliquot of europium-labeled anti-phosphotyrosine ($Eu^{3+}$-PT66, Wallac CR04-100) diluted in 50 mM Tris-HCl, pH 7.8, 150 mM NaCl, 10 μM DTPA, 0.05% Tween 40, 0.2% BSA, 0.05% BGG (1 nM final conc.) is added to each well and incubated for 30 min at room temperature. Upon completion of the incubation, the plate is washed four times with 100 μL of wash buffer and 50 μL of DELFIA Enhancement Solution (Wallac) is added to each well. After 15 min, time-resolved fluorescence is measured on the LJL's Analyst (excitation at 360 nm, emission at 620 nm, EU 400 Dichroic Mirror) after a delay time of 250 μs.

Preferred compounds of the invention have an activity of 1 microMolar or less.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the schemes below are either commercially available or easily prepared from commercially available materials by those skilled in the art.

GENERAL SYNTHETIC METHODS

The invention also provides processes for making compounds of formula I. In all schemes, unless specified otherwise, R substituents in the formulas below shall have the meaning of R substituents in the formula I of the invention described herein above. Intermediates used in the preparation of compounds of the invention are either commercially available or readily prepared by methods known to those skilled in the art.

Compounds of formula I may be prepared by the method outlined in Scheme 1.

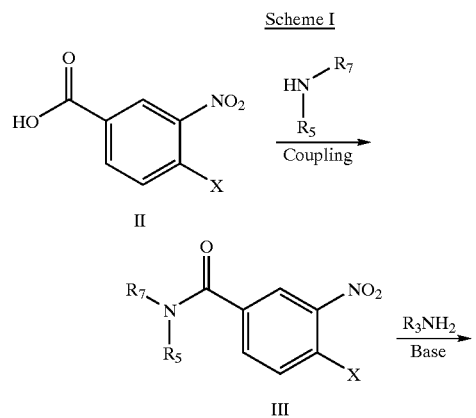

According to this method, a nitrobenzoic acid (II) bearing a leaving group, X, ortho to the nitro group is coupled with an amine bearing $R_5$ and $R_7$. Suitable leaving groups include halogens, preferably fluorine. Standard coupling conditions known in the art may be used, for example reacting II and the amine in the presence of a coupling reagent such as 1-(3-dimethylaminopropyl)-3-ethylcarbodiimide (EDC) in a suitable solvent such as methylene chloride. The resulting intermediate III is then reacted with an amine bearing $R_3$, in the presence of a suitable base such as triethylamine, in a suitable solvent such as DMSO to provide IV. If desired, one may perform this step prior to the coupling of $R_5R_7NH$ to the benzoic acid II. The nitro group of IV is then reduced using methods known in the art such as catalytic hydrogenation. Suitable catalysts include platinum or palladium on carbon. The reaction is run in a suitable solvent such as EtOH either under hydrogen atmosphere or in the presence of a hydrogen source such as ammonium formate. The resulting aniline is then cyclized by treatment with cyanogen bromide in a suitable solvent such as EtOH to provide the 2-aminobenzimidazole VI. Acylation of VI with an acyl halide bearing $R_2$ provides the desired product of formula I. Further modification of the R substituents by standard methods could provide additional desired products of formula I. Compounds of formula I having $R_4$ in the 6-position may be prepared analogously starting with the p-nitrobenzoic acid derivative corresponding to II.

The synthesis of 2-aminobenzimidazoles using solid phase chemistry has been reported (J. Lee et al., Tetrahedron Letters, 2001, 42, 2635–2638). If desired, one may use solid phase chemistry techniques to prepare compounds of formula I as illustrated in Scheme 2 and described below. As is known in the art, after each of the steps described below, the reaction vessel is drained and the resin washed with solvents such as DMF followed by MeOH and methylene chloride. Completion of each step may be monitored by techniques known in the art such as a ninhydrin test or cleavage of a small sample of resin and analysis by LC-MS.

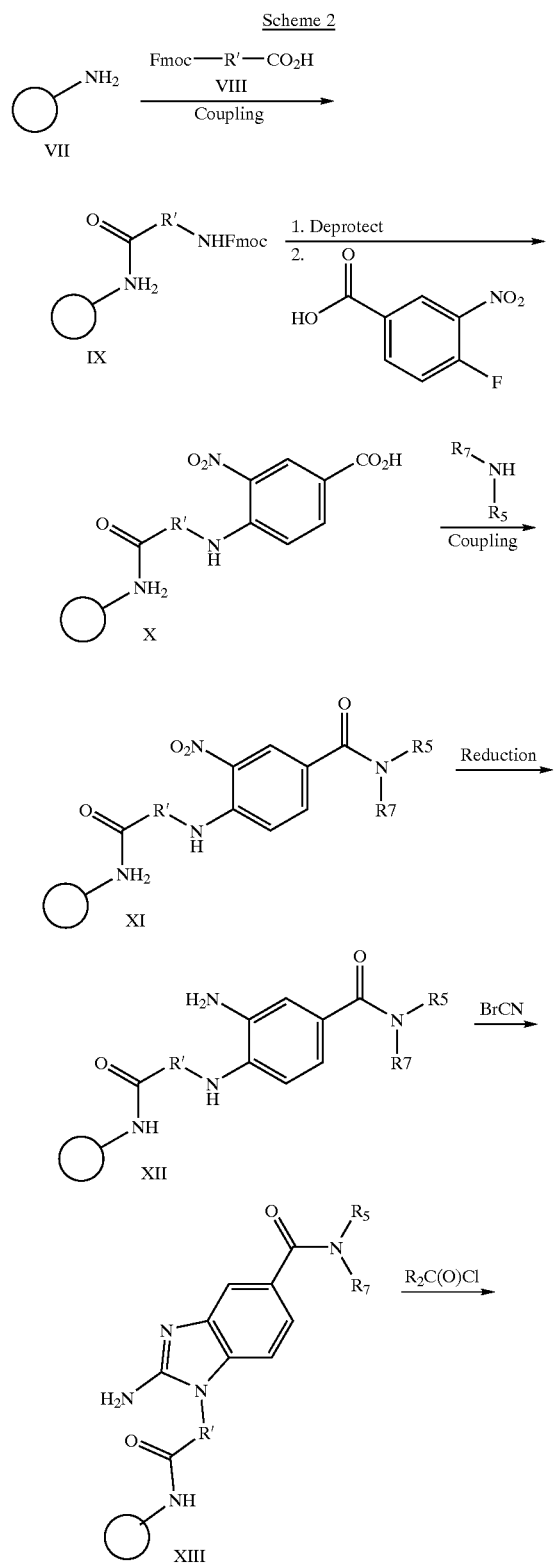

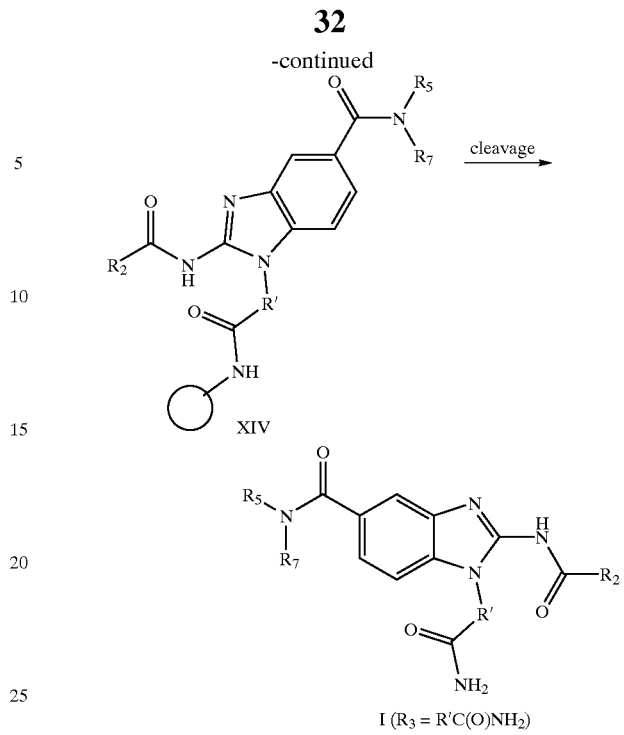

Using this approach, one starts with a suitable amine-bearing resin such as Sieber Amide resin (VII). An Fmoc-protected amino acid (VIII) is coupled to the amine on the resin using a coupling reagent such as 1,3-diisopropylcarbodiimide (DIC) or O-(1H-benzotriazol-1-yl)-N,N,N',N'-tetramethyluronium tetrafluoroborate (TBTU), in the presence of a suitable base such as diisopropylethylamine, in a suitable solvent such as DMF to provide IX. The Fmoc protecting group is removed by treating the resin with about 20% to 50% piperidine in DMF. Deprotection is followed by treatment with 4-fluoro-3-nitrobenzoic acid in the presence of a suitable base such as diisopropylethylamine, in a suitable solvent such as DMSO to provide X. An amine bearing $R_5$ and $R_7$ is then coupled to the carboxylic acid of X using coupling conditions amenable to solid phase synthesis, such as reacting $R_5R_7NH$ with X in the presence of bromo-tris-pyrrolidino-phosphonium hexafluorophosphate and diisopropylethylamine in DMF, to provide XI.

The nitro group on XI is then reduced using conditions suitable for solid phase synthesis, such as treatment of XI with about a 1 M to 2 M $SnCl_2$ hydrate solution in DMF, to provide XII. Treatment of XII with about a 1 M solution of cyanogen bromide in a suitable solvent such as 1:2 to 1:3 EtOH:DMF provides the resin-linked 2-aminobenzimidazole XIII. Treatment of XIII with $R_2C(O)Cl$ in the presence of a suitable base such as diisopropylethylamine and dimethylaminopyridine, in a suitable solvent such as methylene chloride provides XIV. Finally, treatment of XIV under cleavage conditions such as a 5% solution of trifluoroacetic acid in methylene chloride, provides the desired product of formula I ($R_3$=—$R'C(O)NH_2$) or a precursor that could be further modified by standard methods known in the art.

SYNTHETIC EXAMPLES

Example 1

Synthesis of 4-{5-(cyclohexyl-methyl-carbamoyl)-2-[(thiophene-2-carbonyl)-amino]-benzimidazol-1-yl}-butyric acid ethyl ester

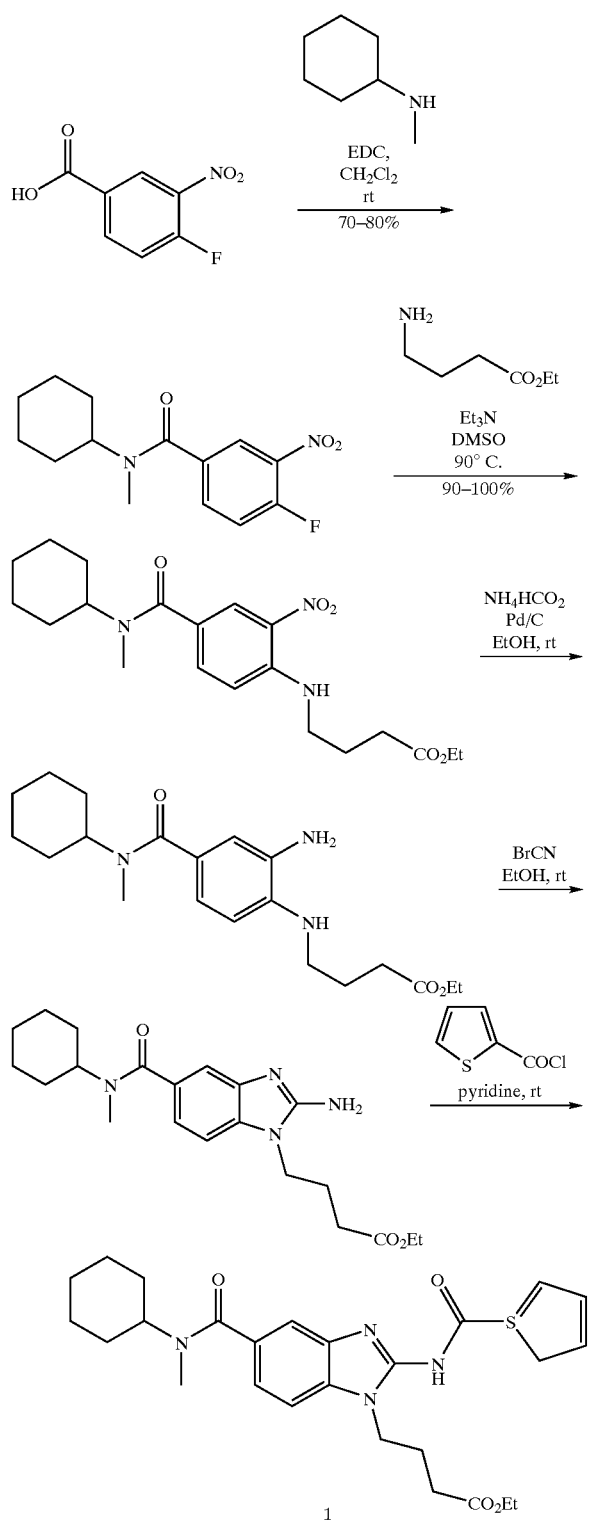

To a solution of 4-fluoro-3-nitrobenzoic acid (6 g, 0.32 mmol) in $CH_2Cl_2$ (30 mL) was added 1-[3-(dimethylamino)propyl]-3-ethylcarbodimide hydrochloride (8 g, 0.42 mmol), followed by N-methylcyclohexylamine (4.2 mL, 0.32 mmol). The mixture was stirred at room temperature for 6 h. The resulting solution was washed in turn with 1N HCl (10 mL) and saturated sodium carbonate (10 mL), and the organic layer was dried over magnesium sulfate. The solvent was evaporated and the resulting oil was purified by flash chromatography with 100% EtOAc to give cyclohexyl-N-methyl-4-fluoro-3-nitro-benzamide (6.0 g, 67%), m.p. 65–67° C.

A stirred solution of the above amide (2 g, 7.1 mmol), ethyl 4-aminobutyrate hydrochloride (2.4 g, 14.2 mmol), and triethylamine (2.5 mL, 18.0 mmol) in DMSO (25 mL) was heated to 80° C. for 8 h. The reaction mixture was poured into a separatory funnel containing dichloromethane (150 mL) and water (150 mL). The organic layer was washed with water (5×50 mL), dried over magnesium sulfate, and the solvent evaporated to give 4-[4-N-cyclohexyl-N-methyl-carbamoyl)-2-nitro-phenylamino]-butyric acid ethyl ester (2.8 g, 100%).

A reaction flask equipped with a nitrogen line and a stir bar was charged with 10% palladium on activated carbon (0.22 g) and EtOH (5 mL). A solution of the above amide (2.2 g, 5.6 mmol) in EtOH (25 mL) was added, followed by ammonium formate (3.9 g, 61.8 mmol), and the mixture was stirred at room temperature for 32 h. The reaction mixture was filtered through diatomaceous earth, washing with EtOH, and the filtrate concentrated to a volume of 25 mL. The resulting solution of 4-[2-amino-4-(N-cyclohexyl-N-methyl-carbamoyl)-phenylamino]-butyric acid ethyl ester was used immediately in the next step.

Cyanogen bromide (0.9 g, 8.4 mmol) was added to the solution obtained above and the resulting solution stirred at room temperature for 24 h. The solvent was evaporated and the residue partitioned between EtOAc (20 mL) and saturated sodium carbonate (10 mL). The organic layer was washed with water (10 mL) and dried over magnesium sulfate. The solvent was evaporated and the resulting purple oil was purified by flash chromatography with 5–50% MeOH/dichloromethane to give 4-[2-amino-5-(cyclohexyl-methyl-carbamoyl)-benzoimidazol-1-yl]-butyric acid ethyl ester (0.7 g, 32%).

To a stirred solution of the above amino benzimidazole (0.7 g, 1.8 mmol) in pyridine (10 mL) was added 2-thiophenecarbonyl chloride (0.41 mL, 3.8 mmol). The reaction was complete in 6 h. The pyridine was evaporated and the resulting orange solid was purified by flash chromatography with 1% MeOH/dichloromethane to give the title compound (0.61 g, 67%), m.p. 82–84° C.

Example 2

Synthesis of 4-{5-(cyclohexyl-methyl-carbamoyl)-2-[(thiophene-2-carbonyl)-amino]-benzimidazol-1-yl}-butyric acid

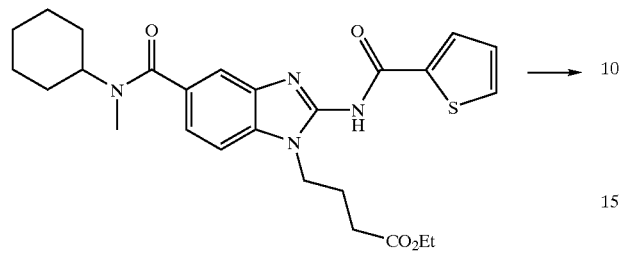

To a stirred solution of 4-{5-(N-cyclohexyl-N-methyl-carbamoyl)-2-[(thiophene-2-carbonyl)-amino]-benzoimidazol-1-yl}-butyric acid ethyl ester (Example 1) (0.5 g, 1.0 mmol) in MeOH (10 mL) and water (10 mL) was added solid NaOH (0.12 g, 3 mmol). The reaction was complete in 4 h. The mixture was acidified with 1N HCl, and was diluted with CH$_2$Cl$_2$ (20 mL). The organic layer was dried over magnesium sulfate, the solvent evaporated and the residue purified by flash chromatography with 10% MeOH/dichloromethane to give the title compound (0.43 g, 92%), m.p. 256–258° C.

Example 3

Synthesis of 1-(3-carbamoyl-propyl)-2-[(thiophene-2-carbonyl)-amino]-1H-benzimidazole-5-carboxylic acid —N-cyclohexyl-N-methyl-amide

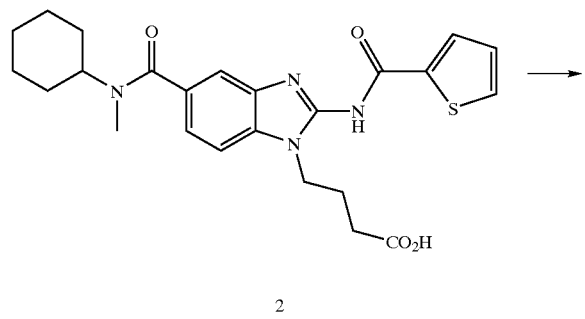

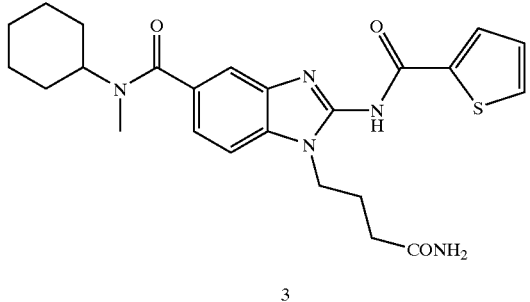

To a solution of 4-{5-(N-cyclohexyl-N-methyl-carbamoyl)-2-[(thiophene-2-carbonyl)-amino]-benzoimidazol-1-yl}-butyric acid (Example 2) (0.05 g, 11 mmol) in DMF (5 mL) was added 1-hydroxybenzotriazole hydrate (0.02 g, 16 mmol) followed by 1-[3-(dimethylamino)propyl]-3-ethylcarbodimide hydrochloride (0.03 g, 16 mmol). The mixture was stirred for 1 h., and ammonium hydroxide (5 mL) was added. Stirring was continued for 48 h. The solution was neutralized with 1M HCl, and partitioned between EtOAc (10 mL) and water (10 mL). The organic layer was washed with saturated sodium carbonate (10 mL) and water (3×10 mL). The solvent was evaporated and the resulting oil was purified by flash chromatography with 5% MeOH/dichloromethane to give the title compound (0.02 g, 40%), m.p. 112–115° C.

Example 4

Synthesis of 1-(3-hydroxy-propyl)-2-(thiophene-2-carbonyl)amino-1H-benzimidazole-5-carboxylic acid cyclohexyl-methyl-amide

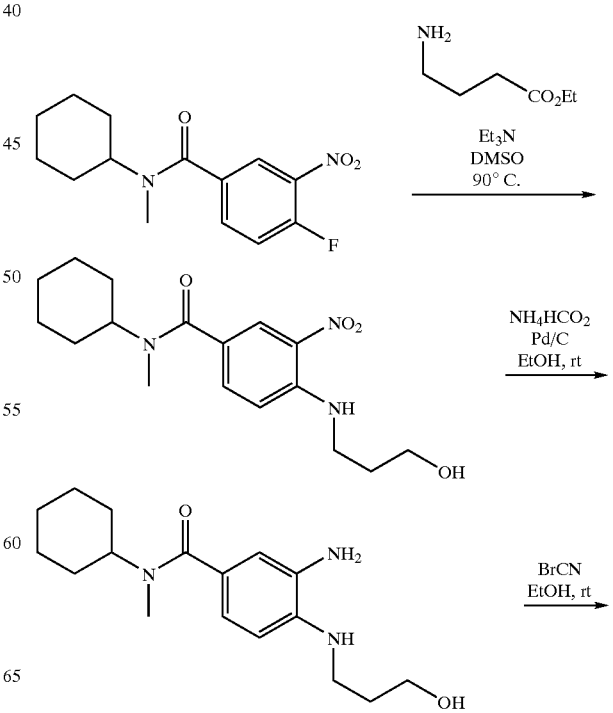

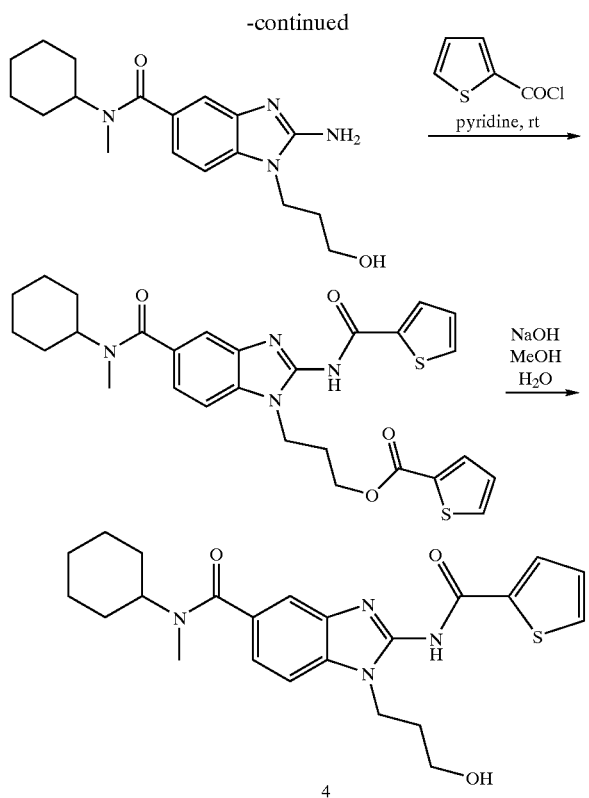

A stirred solution of N-cyclohexyl-N-methyl-4-fluoro-3-nitro-benzamide (Example 1) (1.5 g, 5.3 mmol) and 3-amino-1-propanol (0.82 mL, 10.7 mmol) in DMSO (25 mL) was heated to 80° C. for 8 h. The reaction mixture was poured into a separatory funnel containing dichloromethane (100 mL) and water (100 mL). The organic layer was washed with water (5×50 mL), dried over magnesium sulfate, and the solvent evaporated to give N-cyclohexyl-4-(3-hydroxy-propylamino)-N-methyl-3-nitro-benzamide (1.9 g, 79%).

A reaction flask equipped with a nitrogen line and a stir bar was charged with 10% palladium on activated carbon (0.19 g) and EtOH (5 mL). A solution of the above amide (1.9 g, 5.7 mmol) in EtOH (15 mL) was added, followed by ammonium formate (3.9 g, 62 mmol), and the mixture was stirred at room temperature for 7 h. The reaction mixture was filtered through diatomaceous earth, washing with EtOH, and the filtrate concentrated to a volume of 15 mL. The resulting solution of 3-amino-N-cyclohexyl-4-(3-hydroxypropylamino)-N-methyl-benzamide was used immediately in the next step.

To the solution obtained above was added cyanogen bromide (0.9 g, 8.6 mmol), and the solution stirred at room temperature for 48 h. The solvent was evaporated and the residue partitioned between EtOAc (20 mL) and saturated sodium carbonate (10 mL). The organic layer was washed with water (10 mL) and dried over magnesium sulfate. The solvent was evaporated and the resulting purple oil was purified by flash chromatography with 5–50% MeOH/dichloromethane to give 2-amino-1-(3-hydroxypropyl)-1H-benzimidazole-5-carboxylic acid N-cyclohexyl-N-methyl-amide (0.7 g, 37%).

To a stirred solution of the above amino benzimidazole (0.7 g, 2.1 mmol) in pyridine (10 mL) was added 2-thiophenecarbonyl chloride (0.68 mL, 6.4 mmol). The reaction was complete in 6 h. The pyridine was evaporated and the resulting orange solid was purified by flash chromatography with 1% MeOH/dichloromethane to give thiophene-2-carboxylic acid 3-{5-(cyclohexyl-methyl-carbamoyl)-2-[(thiophene-2-carbonyl)-amino]-benzoimidazol-1-yl}-propyl ester (0.50 g, 43%), m.p. 92–94° C.

To a stirred solution of the above propyl ester (0.4 g, 0.72 mmol) in MeOH (5 mL) and water (5 mL) was added solid NaOH (0.12 g, 2.9 mmol). The reaction was complete in 6 h. The mixture was acidified with 1 M HCl, and was diluted with EtOAc (10 mL). The organic layer was dried over magnesium sulfate, the solvent evaporated and the residue purified by flash chromatography with 5% MeOH/dichloromethane to give the title compound (0.09 g, 28%), m.p. 105–107° C.

Example 5

Synthesis of Acetic Acid 3-{5-(cyclohexyl-methyl-carbamoyl)-2-[(thiophene-2-carbonyl)-amino]-benzoimidazol-1-yl}-propyl ester To a solution of 1-(3-hydroxy-propyl)-2-[(thiophene-2-carbonyl)-amino]-1H-benzoimidazole-5-carboxylic acid cyclohexyl-methyl-amide (Example 4) (0.07 g, 0.16 mmol) in THF (10 mL) was added acetic anhydride (0.02 mL, 0.19 mmol), followed by triethylamine (0.02 mL, 0.17 mmol), and the mixture was stirred at room temperature for 48 h. The resulting solution was washed with 1M HCl (10 mL) and the organic layer was dried over magnesium sulfate. The solvent was evaporated and the resulting oil was purified by flash chromatography with 5% MeOH/dichloromethane to give the title compound (0.05 g, 65%), m.p. 74–76° C.

The following example illustrates the synthesis of a compound of formula I using solid phase chemistry techniques.

Example 6

Synthesis of 2-benzoylamino-1-(carbamoyl-ethyl)-1H-benzimidazole-5-carboxylic acid cyclohexylmethyl-amide Sieber Amide resin (100 mg, 0.52 mmol/g, 0.052 mmol) was added to a solid-phase shaker vessel. DMF (20 mL) was then added and the resin swelled for 10 min prior to reagent addition. TBTU (83 mg, 0.26 mmol) and N,N-diisopropylethylamine (90 microL, 0.52 mmol) were added in one portion and then Fmoc-beta-alanine (81 mg, 0.26 mmol) was also added. The vessel was then agitated for 24 h at room temperature. The vessel was drained and the resin was washed three times with DMF, MeOH, and methylene chloride (20 mL portions, 10 min). A ninhydrin test at this point was negative indicating reaction completion.

The Fmoc group was removed under standard deprotection conditions: 20 mL of a 1:1 DMF:piperdine solution was added to the above resin. The mixture was agitated for 3 h at room temperature and then drained and washed three times with DMF, MeOH, and methylene chloride (20 mL portions, 10 min). A ninhydrin test at this point was positive indicating removal of the FMOC protecting group.

The above resin was then swelled in DMSO (20 mL) for 10 min. To this resin was added 4-fluoro-3-nitrobenzoic acid (48 mg, 0.26 mmol) and N,N-Diisopropylethylamine (90 microL, 0.52 mmol). The vessel was then agitated for 24 h at room temperature. The vessel was drained and the resin was washed two times with DMF, once with DMF:H₂O (1:1), and three times with methylene chloride (20 mL portions). A ninhydrin test at this point was negative indicating reaction completion.

The resin was then swelled for 10 min in DMF (20 mL). To this swelled resin was added bromo-tris-pyrrolidino-phosphonium hexafluorophosphate (PyBroP) (121 mg, 0.26 mmol), diisopropylethylamine (90 microL, 0.52 mmol), and N-methylcyclohexylamine (34 microL, 0.26 mmol). The vessel was then agitated for 24 h at room temperature. The vessel was drained and the resin was washed three times with DMF, MeOH, and methylene chloride (20 mL portions, 10 min). A small aliquot of the resin was then cleaved and analyzed by LC-MS to ensure reaction completion.

To this resin was added a 2.0 M solution of $SnCl_2$ hydrate in DMF (20 mL). The vessel was then agitated for 24 h at room temperature. The vessel was drained and the resin was washed three times with DMF, MeOH, and methylene chloride (20 mL portions, 10 min). A small aliquot of the resin was then cleaved and analyzed by LC-MS to ensure reaction completion.

To this resin was added a 1.0 M solution of BrCN in 1:3 EtOH:DMF (20 mL). The vessel was then agitated for 24 h at room temperature. The vessel was drained and the resin was washed three times with DMF, MeOH, and methylene chloride (20 mL portions, 10 min). A small aliquot of the resin was then cleaved and analyzed by LC-MS to ensure reaction completion.

The resin was then swelled for 10 min in methylene chloride (20 mL). To this swelled resin was added 4-dimethylaminopyridine (31 mg, 0.26 mmol), diisopropylethylamine (90 microL, 0.52 mmol), and benzoyl chloride (30 microL, 0.26 mmol). The vessel was then agitated for 6 h at room temperature. The vessel was drained and the resin was washed three times with DMF, MeOH, and methylene chloride (20 mL portions, 10 min). A cleavage solution of 5% TFA in methylene chloride (20 mL) was then added, agitated for 3 h at room temperature, and the solution collected and concentrated in vacuo to afford the product as a yellow oil. Typical crude purity was >90%. Purification was accomplished by use of preparative TLC using 3% EtOH in methylene chloride to afford the title compound as an off-white solid.

We claim:

1. A compound of the formula (I):

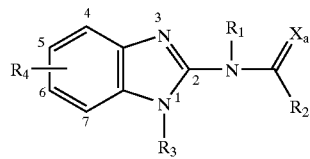

(I)

wherein:

$R_1$ is hydrogen or alkyl;

$R_2$ is chosen from aryl and heteroaryl each $R_2$ is optionally substituted with one or more $R_a$;

$R_3$ is $C_{1-10}$ alkyl chain branched or unbranched optionally substituted with one or more $R_b$, or $R_3$ is the group:
—$(CH_2)_n$-L-$R_6$, wherein L is chosen from a bond, —NH—C(O)—, —O—C(O)—, —C(O)—and —S(O)$_m$ wherein m is 0, 1 or 2, and wherein said group is optionally substituted by one or more $R_b$;
wherein $R_6$ is independently chosen from hydroxy, alkyl, alkoxy, alkylthio, aryl$C_{0-5}$ alkyl, aryloxy$C_{0-5}$ alkyl, heteroaryl$C_{0-5}$ alkyl, cycloalkyl$C_{0-5}$ alkyl, heterocyclyl$C_{0-5}$ alkyl and amino said amino is optionally mono-or di-substituted by acyl, alkyl, alkoxycarbonyl, cycloalkyl$C_{0-5}$ alkyl, aryl$C_{0-5}$ alkyl, heteroaryl$C_{0-5}$ alkyl or heterocyclyl$C_{0-5}$ alkyl;

n is 1–10;

$R_4$ is the group:

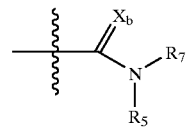

wherein $R_4$ is covalently attached at the indicated 5- or 6-position of the formula (I);

$R_5$ is chosen from aryl$C_{0-5}$ alkyl, heteroaryl$C_{0-5}$ alkyl, cycloalkyl$C_{0-5}$ alkyl and heterocyclyl$C_{0-5}$ alkyl, each $R_5$ optionally substituted with one or more $R_c$;

$R_7$ is hydrogen, alkenyl or alkyl;

or $R_5$ and $R_7$ together with the nitrogen atom to which they are attached form:

a 4-7-membered monocyclic ring or an 8-14-membered bicyclic ring, wherein each monocyclic or bicyclic ring optionally contains an additional 1 to 3 heteroatoms chosen from N, O and S and each ring is aromatic or nonaromatic, and wherein each monocyclic or bicyclic ring is optionally substituted by one or more $R_c$;

each $R_a$, $R_b$ or $R_c$ are independently chosen from hydrogen, alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-or-di-substituted by alkyl, acyl or alkoxycarbonyl, wherein any of the above $R_a$, $R_b$ or $R_c$ are optionally halogenated where possible; and $X_a$ and $X_b$ are oxygen or sulfur;

or the pharmaceutically acceptable salts, esters, isomers or tautomers thereof.

2. The compound according to claim 1 wherein $R_1$ is hydrogen;

$R_2$ is chosen from phenyl, naphthyl, and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl each $R_2$ is optionally substituted with one or more $R_a$;

$R_3$ is $C_{1-10}$ alkyl chain branched or unbranched optionally substituted with one or more $R_b$, or $R_3$ is:
—$(CH_2)_n$-L-$R_6$, wherein L is chosen from a bond, —O—C(O)—, —C(O)—and —S(O)$_m$-wherein m is 0, 1 or 2, and wherein said group is optionally substituted by one or more $R_b$, wherein $R_6$ is independently chosen from hydroxy, $C_{1-5}$ alkyl, $C_{1-5}$ alkoxy, $C_{1-5}$ alkylthio, phenyl, naphthyl, benzyl, phenethyl, heteroaryl$C_{0-5}$ alkyl, $C_{3-7}$ cycloalkyl$C_{0-5}$ alkyl, heterocyclyl$C_{0-5}$ alkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl, heteroaryl$C_{0-5}$ alkyl or heterocyclyl$C_{0-5}$ alkyl; and wherein each recited heteroaryl in this paragraph is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl and wherein each recited heterocyclyl in this paragraph is chosen from pyrrolidinyl, morpholinyl, thiomorpholinyl, dioxalanyl, piperidinyl and piperazinyl;

$R_5$ is chosen from phenyl, naphthyl, benzyl, phenethyl, heteroaryl$C_{0-5}$ alkyl wherein the heteroaryl is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl, $C_{3-7}$ cycloalkyl$C_{0-5}$ alkyl and heterocyclyl$C_{0-5}$ alkyl wherein the heterocyclyl is chosen from aziridinyl, pyrrolidinyl, morpholinyl, thiomorpholinyl, tetrahydrofuranyl, dioxalanyl, piperidinyl and piperazinyl, each $R_5$ is optionally substituted with one or more $R_c$;

each $R_a$, $R_b$ or $R_c$ are independently chosen from hydrogen, $C_{1-5}$ alkyl, $C_{2-5}$ alkenyl, $C_{2-5}$ alkynyl, $C_{3-8}$ cycloalkyl, phenyl, benzyl, phenoxy, $C_{1-5}$ alkoxy, $C_{1-5}$ alkylthio, $C_{1-5}$ acyl, $C_{1-5}$ alkoxycarbonyl, $C_{1-5}$ acyloxy, $C_{1-5}$ acylamino, $C_{1-5}$ sulphonylamino, aminosulfonyl, $C_{1-5}$ alkylsulfonyl, carboxy, carboxamide, hydroxy, halogen, trifluoromethyl, nitro, nitrile and amino optionally mono-or-di-substituted by $C_{1-5}$ alkyl, $C_{1-5}$ acyl or $C_{1-5}$ alkoxycarbonyl, wherein any of the above $R_a$, $R_b$ or $R_c$ are optionally halogenated where possible;

$R_7$ is $C_{3-10}$ alkenyl or $C_{1-5}$ alkyl; and $X_a$ and $X_b$ are oxygen.

3. The compound according to claim 2 wherein $R_2$ is chosen from phenyl, naphthyl and heteroaryl chosen from thienyl, furanyl, isoxazolyl, oxazolyl, imidazolyl, thiadiazolyl, pyrazolyl, pyridinyl, quinoxalinyl and benzothienyl each $R_2$ is optionally substituted with one or more $R_a$;

$R_6$ is independently chosen from hydroxy, $C_{1-5}$ alkyl, $C_{1-5}$ alkoxy, phenyl, benzyl, phenethyl, heteroaryl$C_{0-5}$ alkyl, heterocyclyl$C_{0-5}$ alkyl, $C_{3-7}$ cycloalkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl or heteroaryl$C_{0-5}$ alkyl;

and wherein each recited heteroaryl in this paragraph is chosen from thienyl, furanyl, isoxazolyl, oxazolyl, thiazolyl, thiadiazolyl, tetrazolyl, pyrazolyl, pyrrolyl and imidazolyl;

n is 1–6;

$R_5$ is chosen from phenyl, naphthyl, benzyl, phenethyl, heteroaryl$C_{0-5}$ alkyl wherein the heteroaryl in this paragraph is chosen from thienyl, furanyl, imidazolyl and pyridinyl, $C_{3-7}$ cycloalkyl$C_{0-5}$ alkyl and heterocyclyl$C_{0-5}$ alkyl wherein the heterocyclyl is chosen from aziridinyl, pyrrolidinyl, tetrahydrofuranyl, tetrahydropyridinyl, morpholinyl, thiomorpholinyl, piperidinyl and piperazinyl, each $R_5$ is optionally substituted with one or more $R_c$; and and $R_7$ is propenyl or $C_{1-3}$ alkyl.

4. The compound according to claim 3 wherein $R_2$ is chosen from phenyl and heteroaryl chosen from thienyl, furanyl, isoxazolyl, thiadiazolyl, pyrazolyl and pyridinyl each $R_2$ is optionally substituted with one or more $R_a$;

$R_3$ is:

—$(CH_2)_n$—C(O)—$R_6$ or

—$(CH_2)_n$—$R_6$;

wherein $R_6$ is independently chosen from hydroxy, $C_{1-5}$ alkyl, $C_{1-5}$ alkoxy, phenyl, thienyl$C_{0-5}$ alkyl, $C_{3-7}$ cycloalkyl and amino said amino is optionally mono- or di-substituted by $C_{1-5}$ alkyl or $C_{1-5}$ alkoxycarbonyl;

$R_5$ is chosen from phenyl, benzyl, phenethyl and $C_{3-7}$ cycloalkyl$C_{0-5}$ alkyl each optionally substituted with one or more $R_c$;

each $R_a$, $R_b$ or $R_c$ are independently chosen from $C_{1-5}$ alkyl, $C_{3-8}$ cycloalkyl, phenyl, $C_{1-5}$ alkoxy, amino optionally mono-or-di-substituted by $C_{1-5}$ alkyl, $C_{1-5}$ alkoxycarbonyl, carboxamide, hydroxy, halogen, trifluoromethyl, nitro and nitric, wherein any of the above $R_a$, $R_b$ or $R_c$ are optionally halogenated where possible;

and $R_7$ is $C_{1-3}$ alkyl.

5. The compound according to claim 4 wherein $R_2$ is chosen from phenyl, thienyl, furanyl, isoxazolyl and pyridinyl each optionally substituted with one or more $R_a$;

$R_5$ is chosen from phenyl and cyclohexyl each optionally substituted with one or more $R_c$; and n is 2–5.

6. The compound according to claim 5 wherein $R_2$ is chosen from phenyl, thien-2-yl, isoxazol-5-yl and pyridin-3-yl each optionally substituted with one or more $R_a$;

$R_6$ is independently chosen from hydroxy, methyl, ethyl, $C_{1-3}$ alkoxy, phenyl, thienyl$C_{0-5}$ alkyl, $C_{3-7}$ cycloalkyl and amino said amino is optionally mono-or di-substituted by $C_{1-5}$ alkyl or $C_{1-5}$ alkoxycarbonyl; and each $R_a$, $R_b$ or $R_c$ are independently chosen from $C_{1-3}$ alkoxy, amino optionally mono-or-di-substituted by $C_{1-3}$ alkyl, carboxamide, hydroxy, fluoro, chloro, bromo, trifluoromethyl, nitro and nitrile.

7. The compound as in any one of claims 1–6 wherein $R_4$ is covalently attached at the indicated 5-position of the formula (1).

8. The compound as in any one of claims 1–6 wherein $R_4$ is covalently attached at the indicated 6-position of the formula (1).

9. A compound chosen from:

-continued
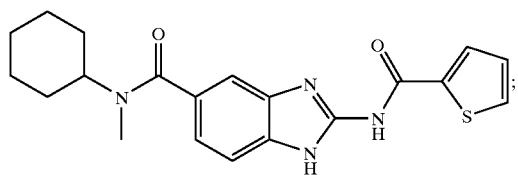
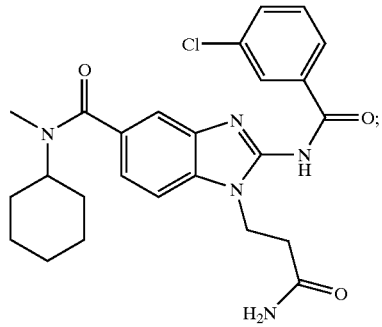
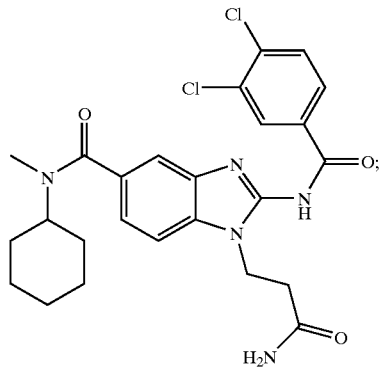
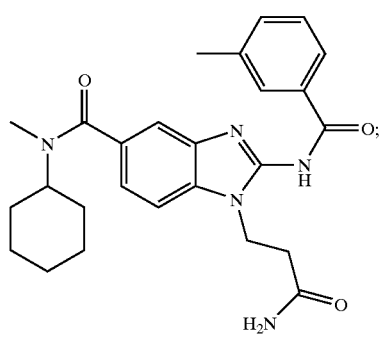
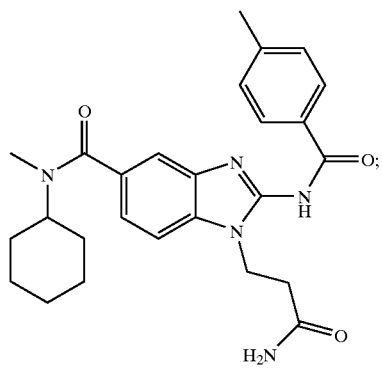
-continued
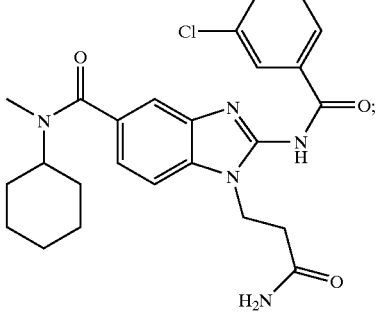

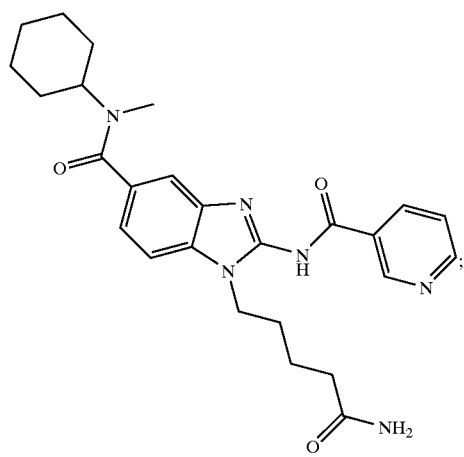
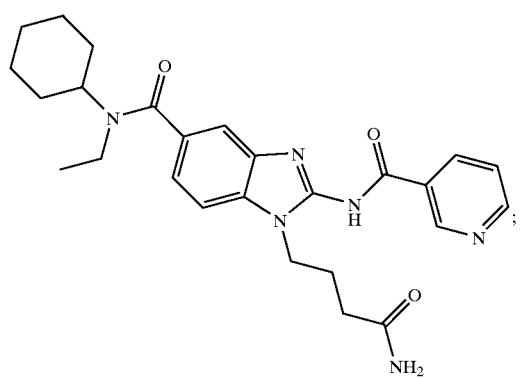
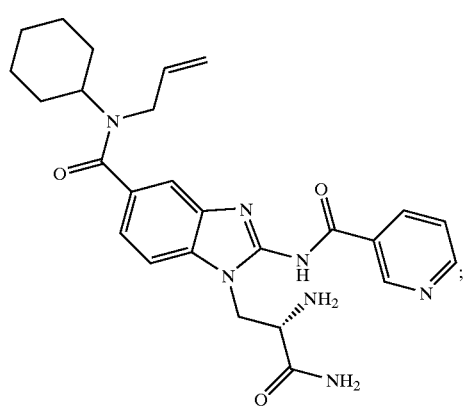
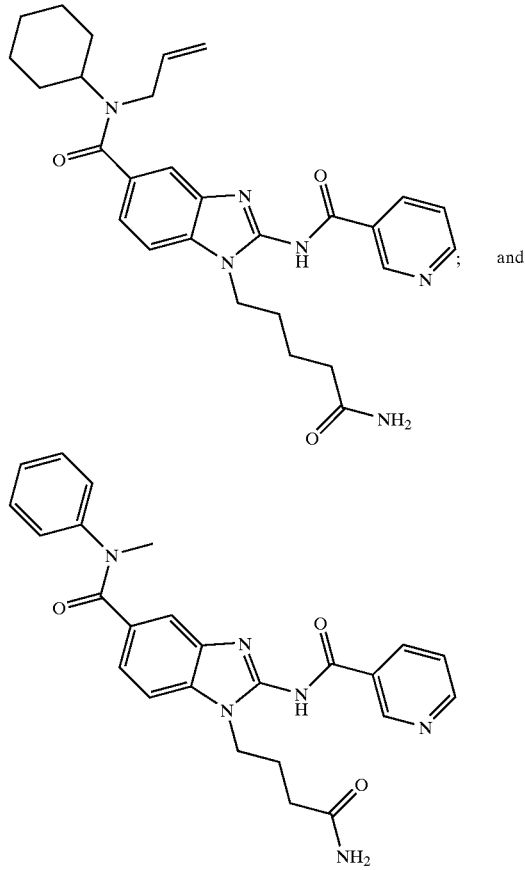
or the pharmaceutically acceptable salts, esters, isomers or tautomers thereof.
10. A compound chosen from:
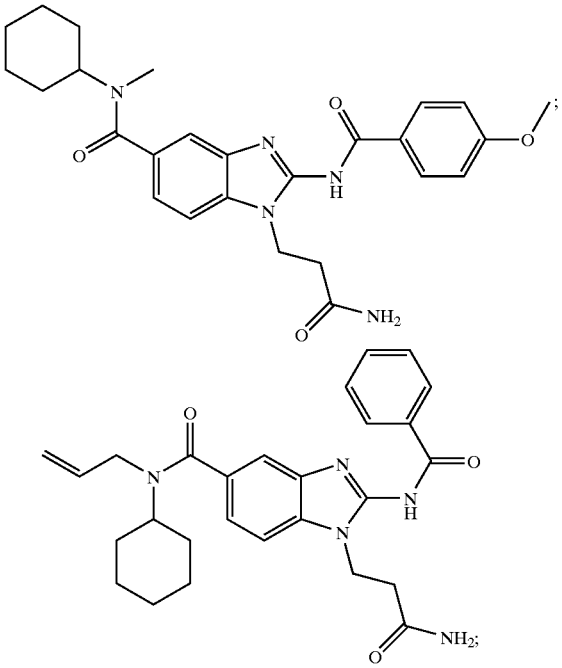

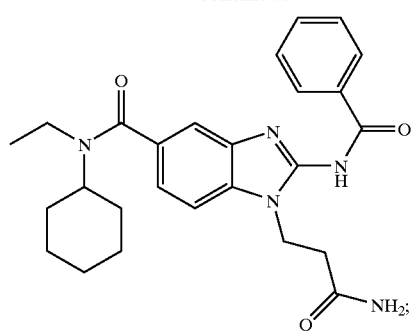
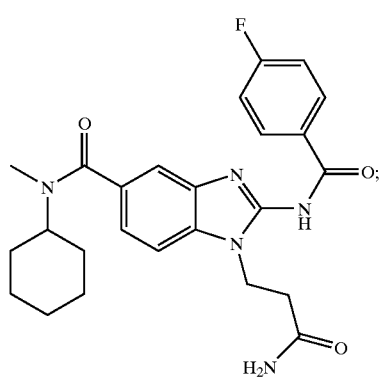
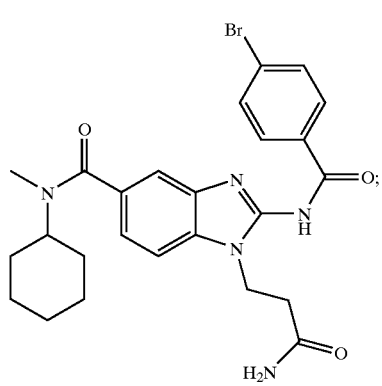
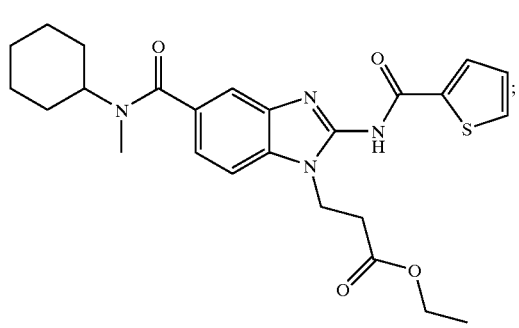
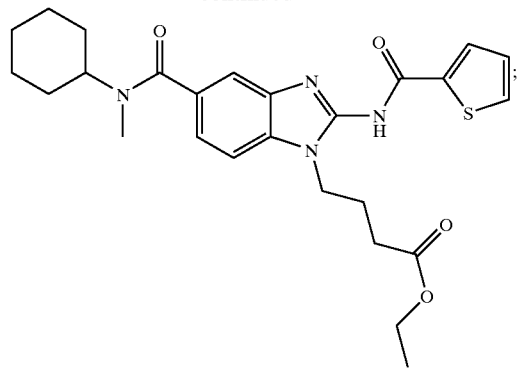
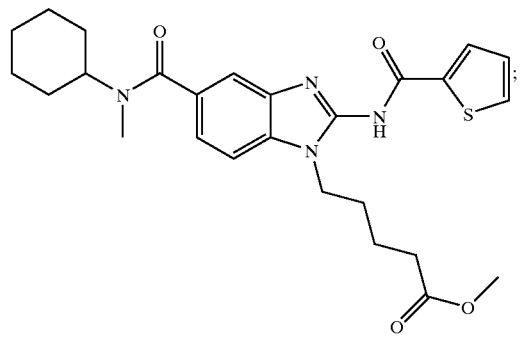
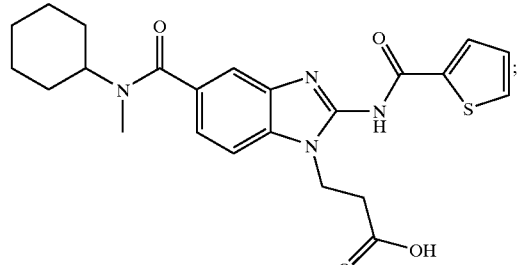
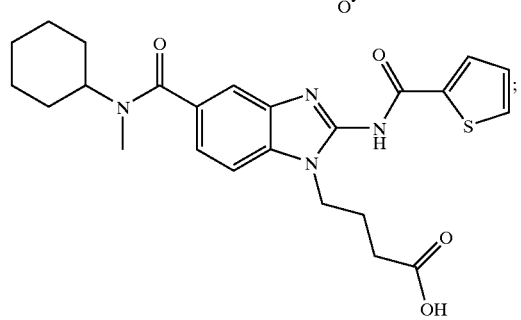
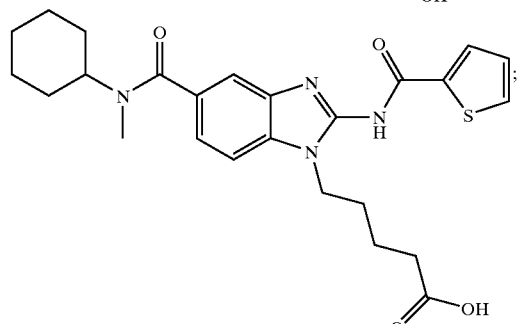

49
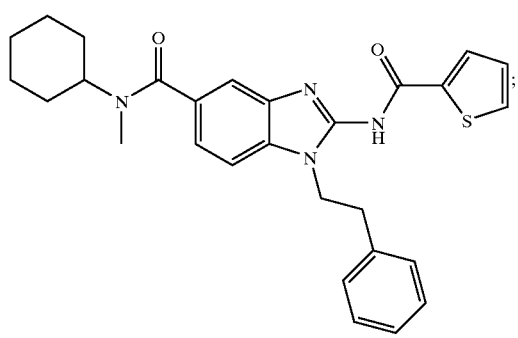
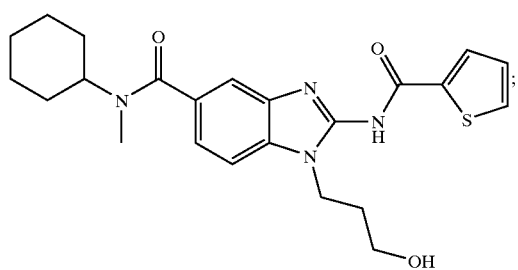
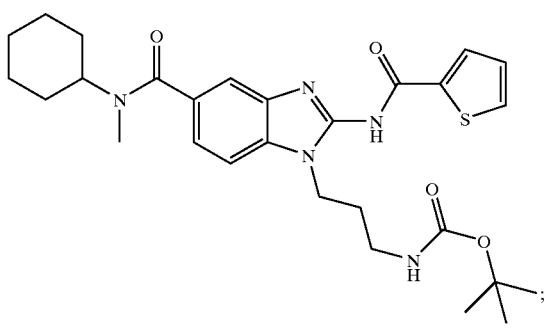
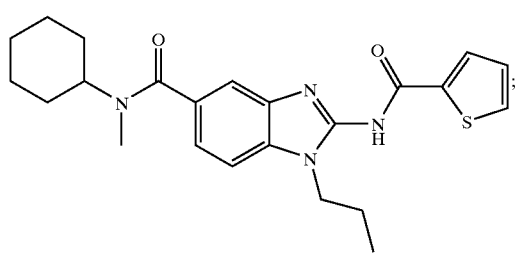
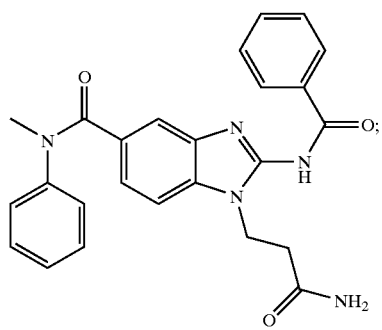
50
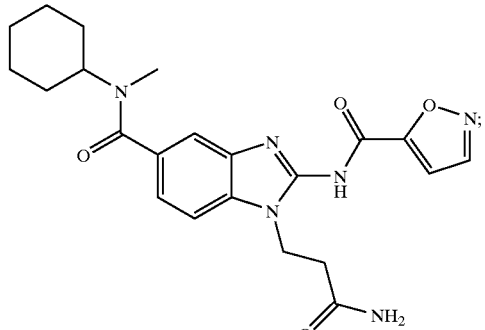
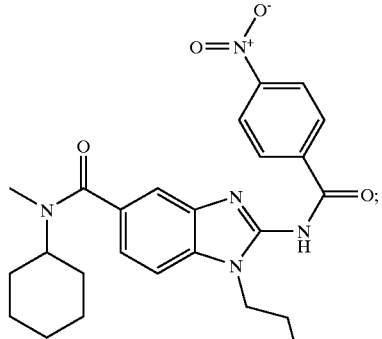
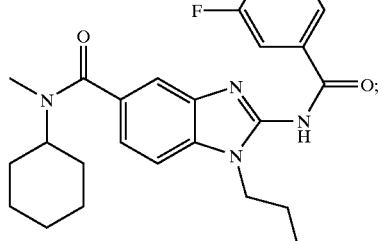
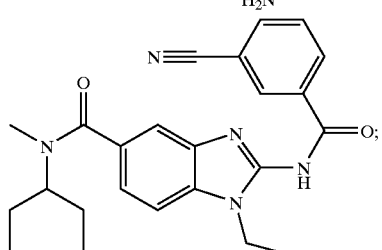
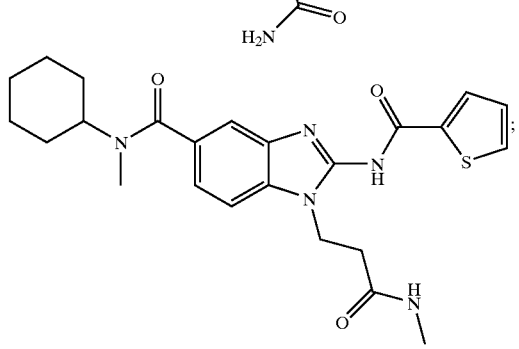

51
-continued
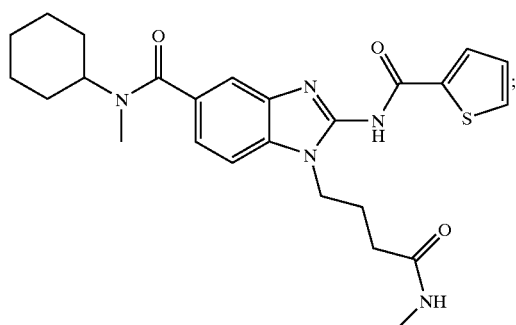
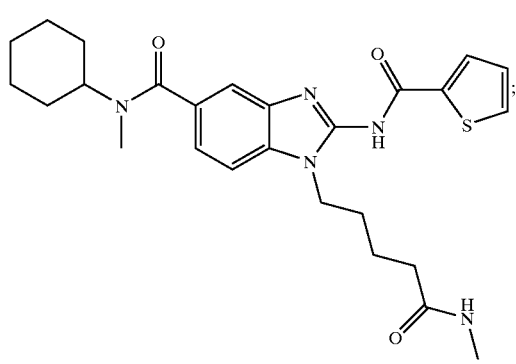
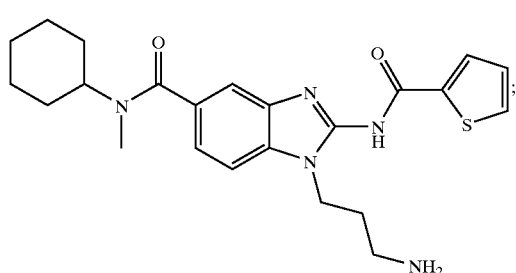
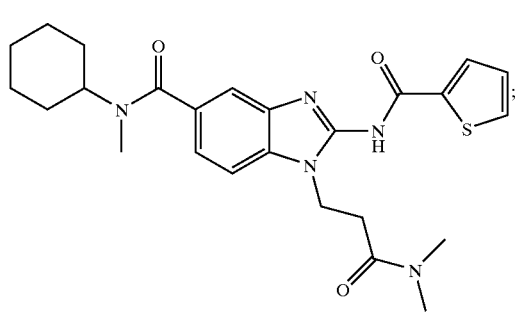
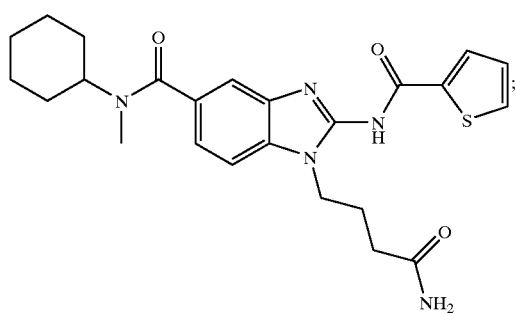
52
-continued
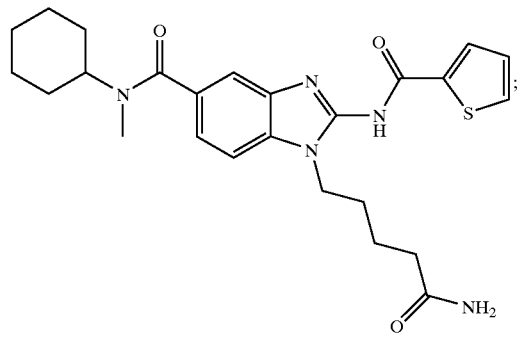
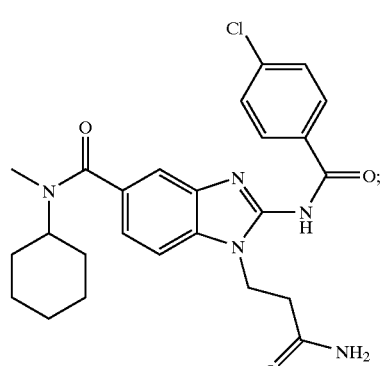
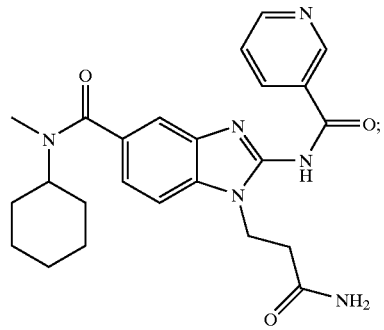
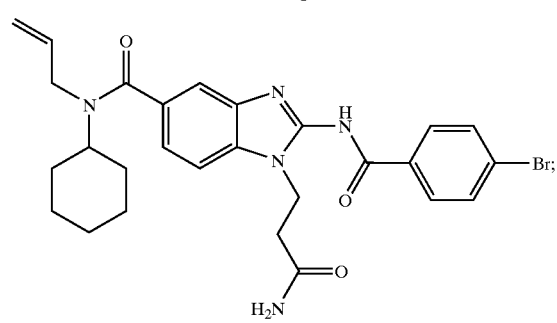
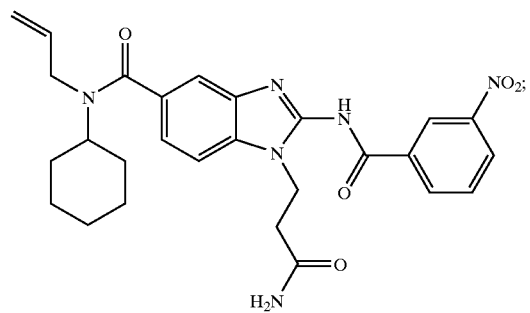

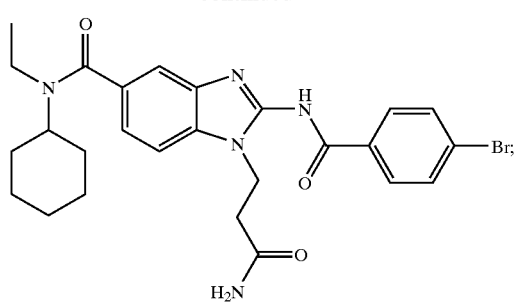
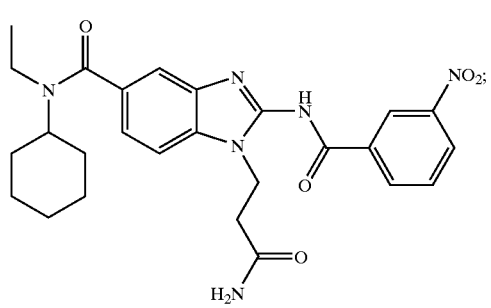
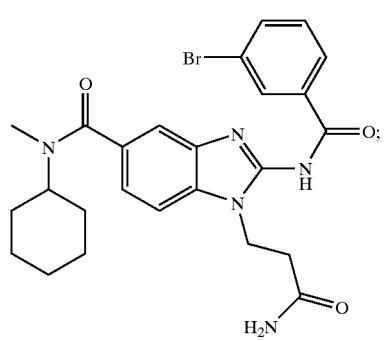
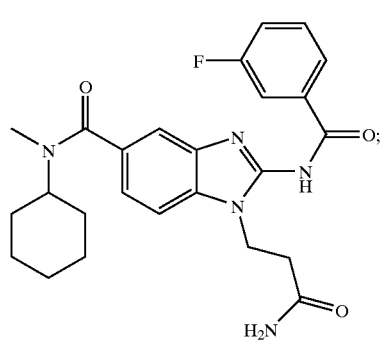
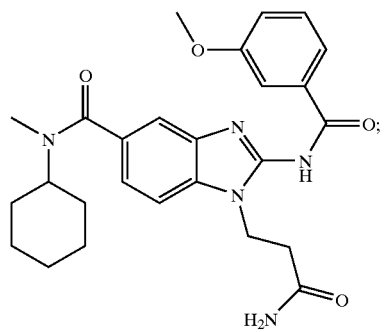
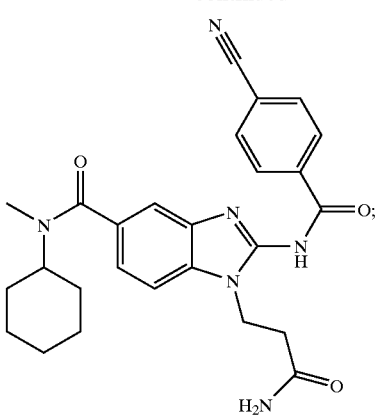
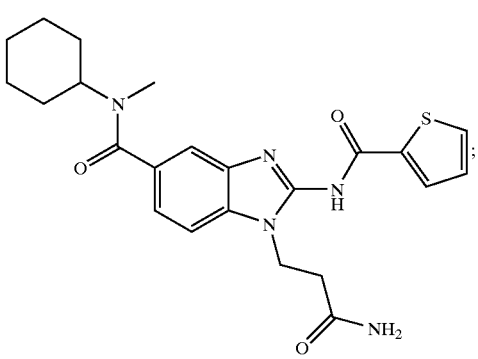
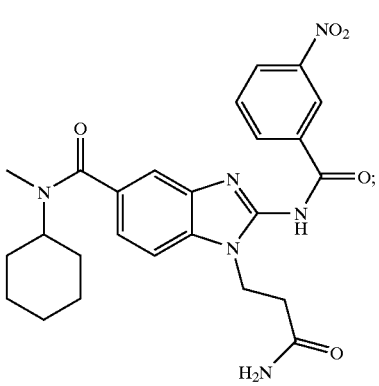
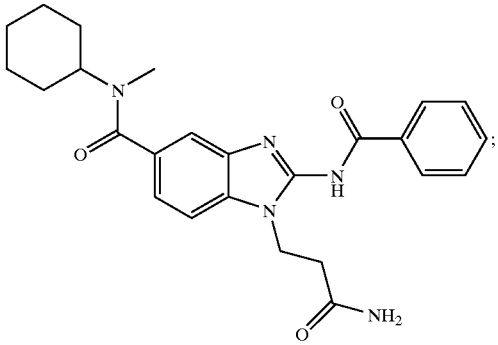

55
-continued
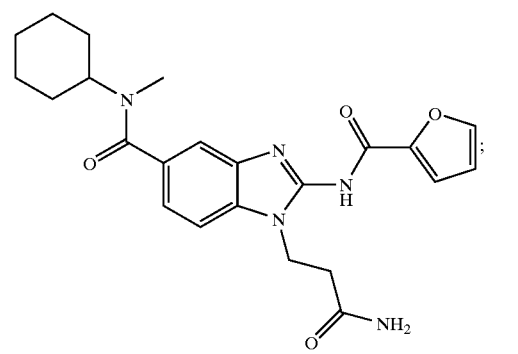
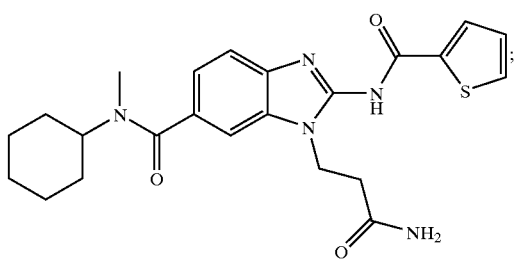
56
-continued
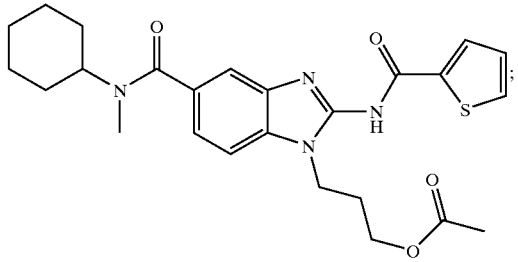
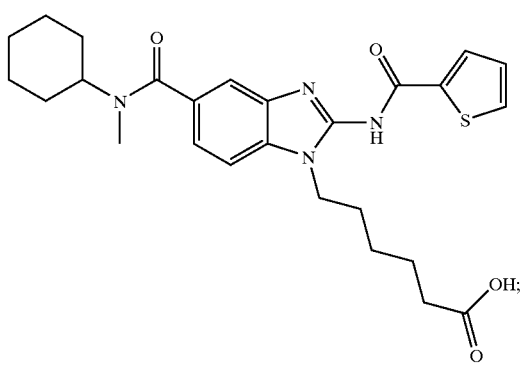
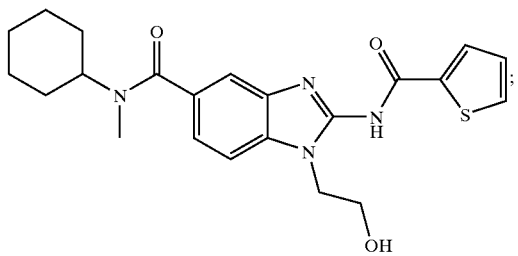
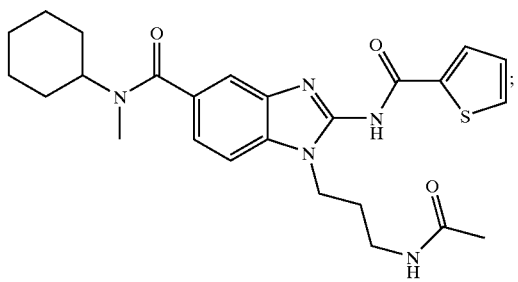

57
-continued
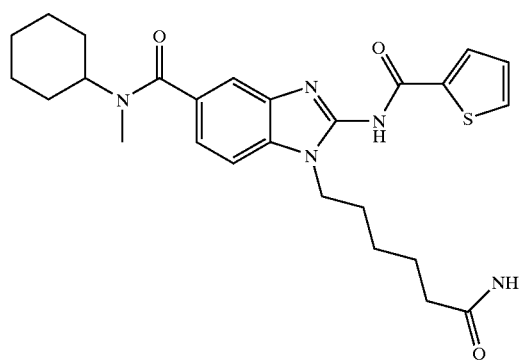
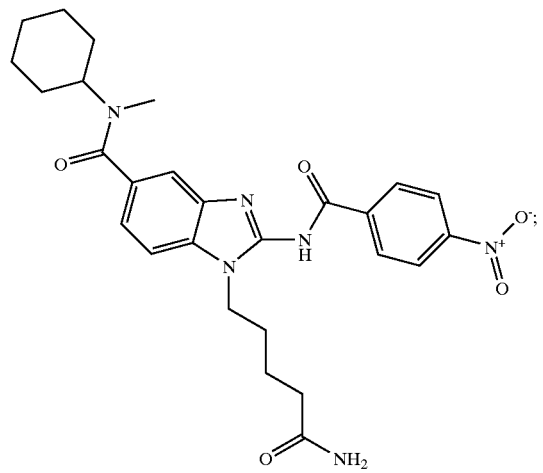
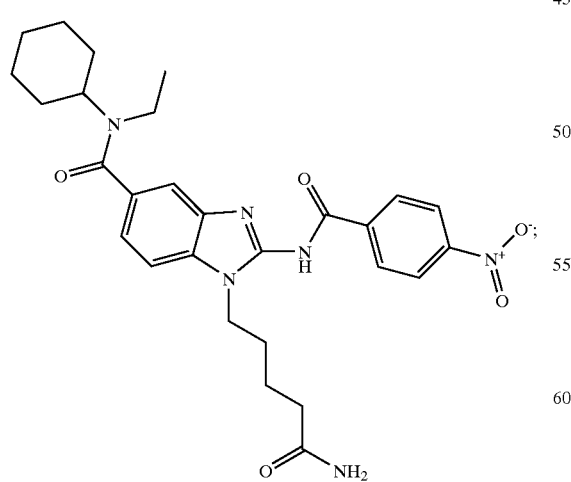
58
-continued
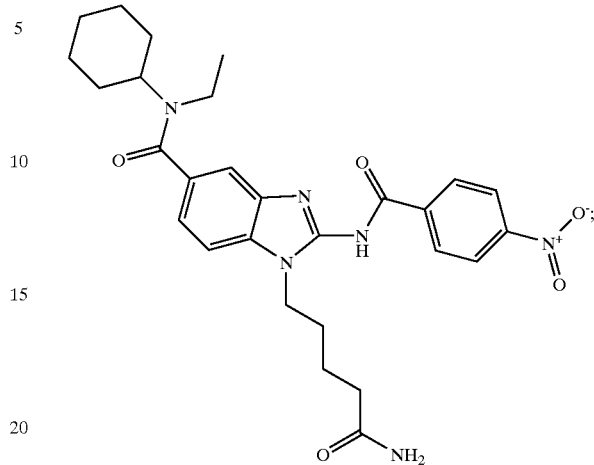
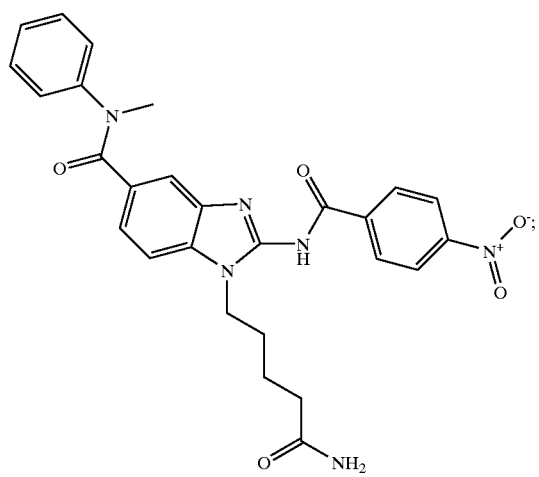
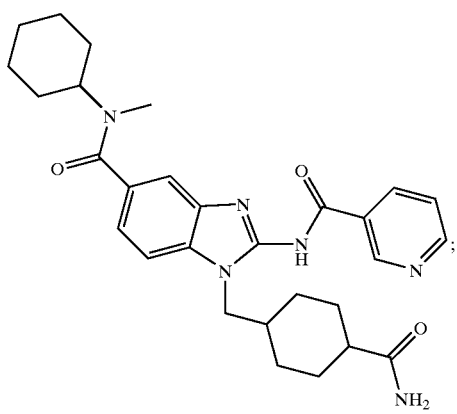

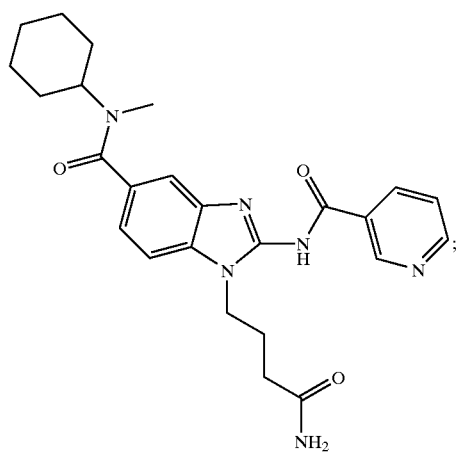
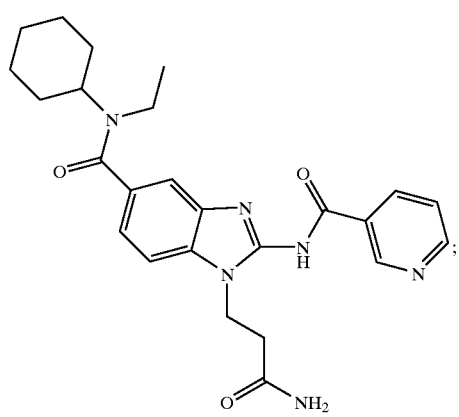
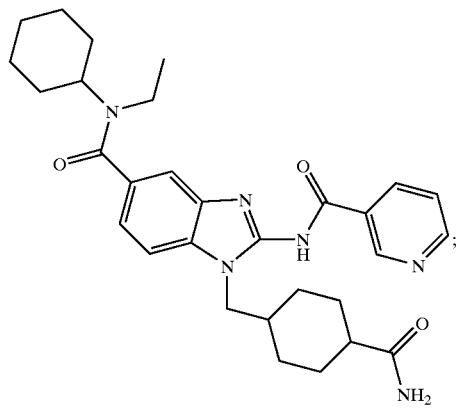
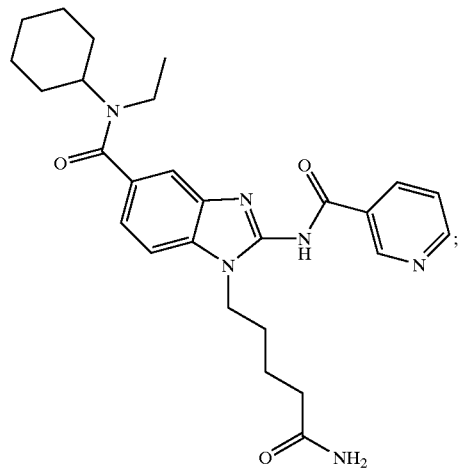
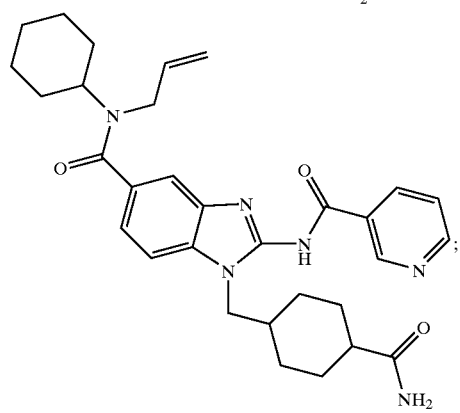
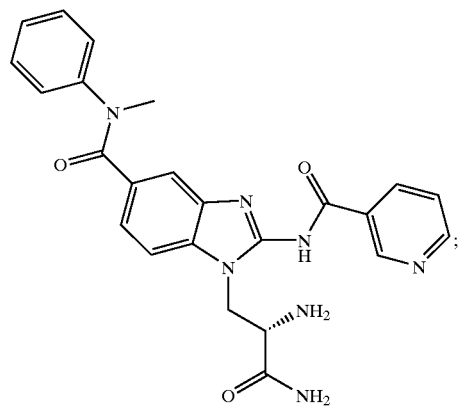 and
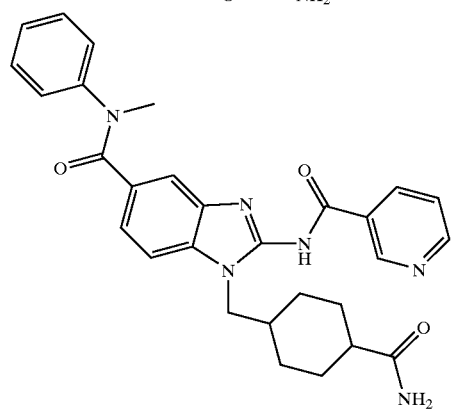

or the pharmaceutically acceptable salts, esters, isomers or tautomers thereof.

11. A pharmaceutical composition comprising a pharmaceutically effective amount of a compound according to claim 1 and one or more pharmaceutically acceptable carriers and/or adjuvants.

12. A method of treating an inflammatory disorder, said method comprising administering to a patient in need thereof a therapeutically effect amount of a compound according to claim 1.

13. A method of treating an allergic disorder said method comprising administering to a patient in need thereof a therapeutically effect amount of a compound according to claim 1.

14. A method of treating a disease chosen from chronic inflammation, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease, lupus erythematosus, asthma, chronic obstructive pulmonary disease (COPD), adult respiratory distress syndrome (ARDS), bronchitis, and allergic rhinitis said method comprising administering to a patient in need thereof a therapeutically effect amount of a compound according to claim 1.

15. A method of making a compound of formula (I) below, wherein $R_2$, $R_3$, $R_5$ and $R_7$ are defined as in claim 1, said method comprising:

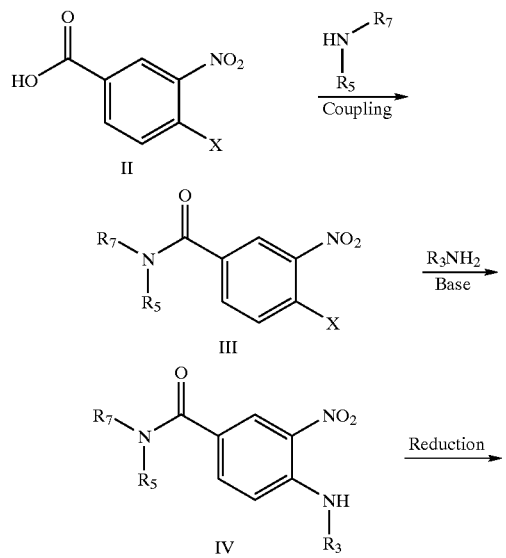

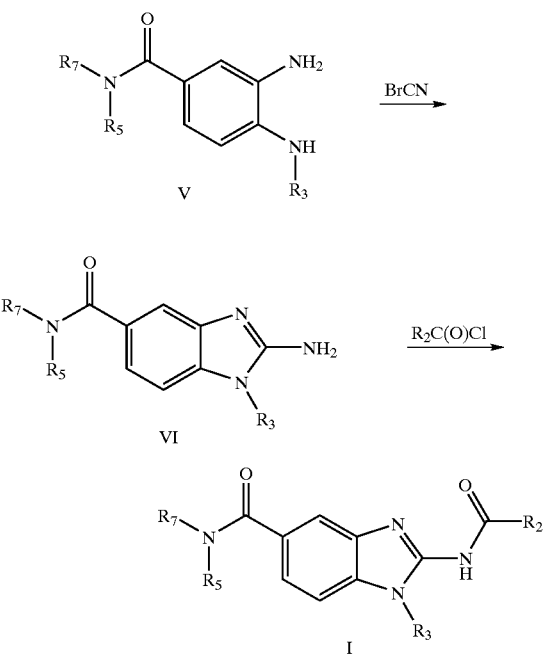

reacting a nitrobenzoic acid (II) wherein X is a leaving group, with an amine bearing $R_5$ and $R_7$ in the presence of a coupling reagent in a suitable solvent to provide compound III;

reacting compound III with an amine bearing $R_3$, in the presence of a suitable base in a suitable solvent to provide compound IV;

reducing the nitro group of IV via catalytic hydrogenation with a suitable catalyst in a suitable solvent either under hydrogen atmosphere or in the presence of a hydrogen source;

cyclizing compound V by treatment with cyanogen bromide in a suitable solvent to provide the 2-aminobenzimidazole VI and acylation of VI with an acyl halide bearing $R_2$ provides the desired product of formula I, and isolating the product.

* * * * *